(12) United States Patent
Guy et al.

(10) Patent No.: US 11,752,111 B2
(45) Date of Patent: Sep. 12, 2023

(54) USE OF CANNABIDIVARIN IN THE TREATMENT OF AUTISM SPECTRUM DISORDER, ASSOCIATED DISORDERS AND SCHIZOPHRENIA

(71) Applicant: GW Research Limited, Cambridge (GB)

(72) Inventors: Geoffrey Guy, Cambridge (GB); Stephen Wright, Cambridge (GB); James Brodie, Cambridge (GB); Marie Woolley-Roberts, Cambridge (GB); Rafael Maldonado, Barcelona (ES); Daniela Parolaro, Varese (IT); Livio Luongo, Naples (IT); Joanna Neill, Manchester (GB)

(73) Assignee: GW RESEARCH LIMITED, Cambridge (GB)

( * ) Notice: Subject to any disclaimer, the term of this patent is extended or adjusted under 35 U.S.C. 154(b) by 694 days.

(21) Appl. No.: 16/092,374

(22) PCT Filed: Apr. 11, 2017

(86) PCT No.: PCT/GB2017/051007
§ 371 (c)(1),
(2) Date: Oct. 9, 2018

(87) PCT Pub. No.: WO2017/178807
PCT Pub. Date: Oct. 19, 2017

(65) Prior Publication Data
US 2019/0160023 A1   May 30, 2019

(30) Foreign Application Priority Data
Apr. 11, 2016 (GB) .................................. 1606098

(51) Int. Cl.
| | | |
|---|---|---|
| *A61K 31/05* | (2006.01) | |
| *A61K 36/185* | (2006.01) | |
| *A61K 45/06* | (2006.01) | |
| *A61K 31/352* | (2006.01) | |
| *A61P 25/28* | (2006.01) | |
| *A61P 25/18* | (2006.01) | |
| *A61K 36/00* | (2006.01) | |

(52) U.S. Cl.
CPC ............ *A61K 31/05* (2013.01); *A61K 31/352* (2013.01); *A61K 36/185* (2013.01); *A61K 45/06* (2013.01); *A61P 25/18* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 10,799,467 B2 | 10/2020 | Whalley et al. | |
| 2006/0194201 A1* | 8/2006 | Fryns ................... | C12Q 1/6883 435/325 |
| 2010/0267733 A1* | 10/2010 | Shytle .................. | A61K 31/352 514/250 |
| 2013/0132114 A1* | 5/2013 | Lombard ............... | G16H 15/00 705/2 |
| 2014/0309270 A1 | 10/2014 | Price | |
| 2015/0342902 A1* | 12/2015 | Vangara ................. | A61K 47/44 514/729 |
| 2016/0002133 A1 | 1/2016 | Mona, III et al. | |

FOREIGN PATENT DOCUMENTS

| | | |
|---|---|---|
| WO | WO 2004/016246 A1 | 2/2004 |
| WO | WO 2006/017892 A1 | 2/2006 |
| WO | WO2008133884 A2 * | 11/2008 |
| WO | WO 2011/121351 A1 | 10/2011 |
| WO | WO2011121351 A1 * | 10/2011 |
| WO | WO 2015/065544 A1 | 5/2015 |

OTHER PUBLICATIONS

Fragile X Clinical and Research Consortium (Nov. 2014, pp. 1-15) (Year: 2014).*
International Search Report for International Application No. PCT/GB2017/051007, Aug. 23, 2017 (six pages).
Written Opinion of the International Searching Authority for International Application No. PCT/GB2017/051007 (eight pages).
International Preliminary Report on Patentability for International Application No. PCT/GB2017/051007, dated Oct. 16, 2018 (9 pages).
Pertwee, Roger G., "Cannabinoid receptor ligands: clinical and neuropharmacological considerations, relevant to future drug discovery and development," Exp. Opin. Invest. Drugs., vol. 9, No. 7, pp. 1-19 (2000).

* cited by examiner

*Primary Examiner* — Michael Barker
*Assistant Examiner* — Randall O Winston
(74) *Attorney, Agent, or Firm* — FINNEGAN, HENDERSON, FARABOW, GARRETT & DUNNER, LLP

(57) ABSTRACT

The present invention relates to the use of cannabidivarin (CBDV) in the treatment of autism spectrum disorder (ASD) and ASD-associated disorders such as Fragile X syndrome (FXS); Rett syndrome (RS); or Angelman syndrome (AS). In a further embodiment the invention relates to the use of CBDV in the treatment of schizophrenia. CBDV has been shown to be particularly effective in improving cognitive dysfunction in rodent models of ASD, FXS, RS, AS and schizophrenia. The CBDV is preferably substantially pure. It may take the form of a highly purified extract of *cannabis* such that the CBDV is present at greater than 95% of the total extract (w/w) and the other components of the extract are characterised. Alternatively, the CBDV is synthetically produced.

18 Claims, 19 Drawing Sheets

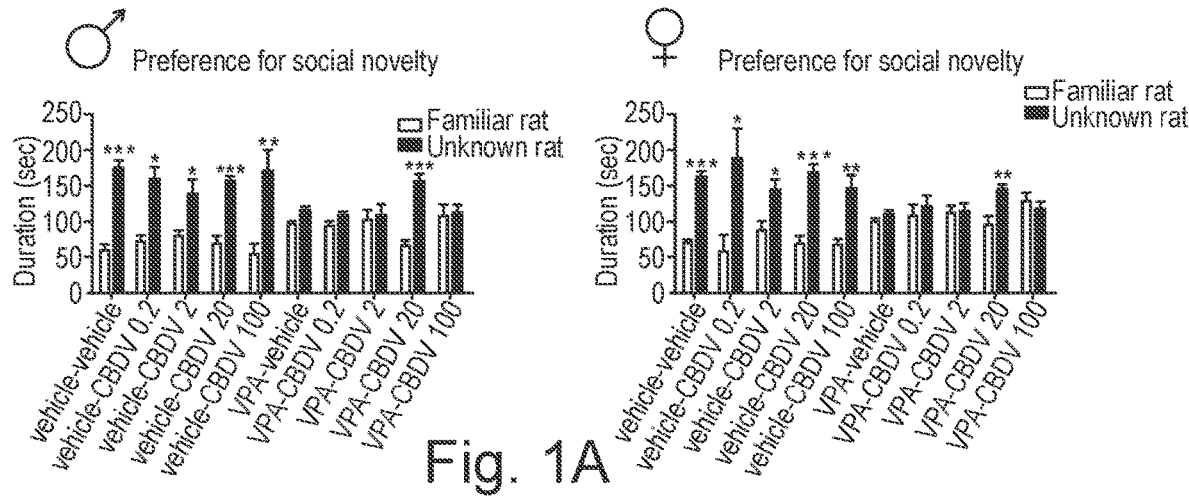
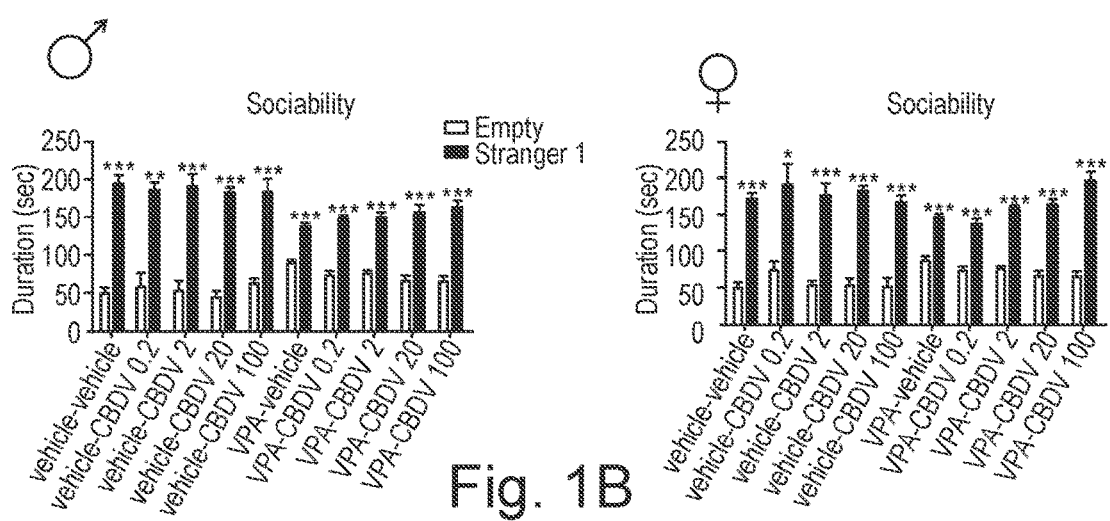
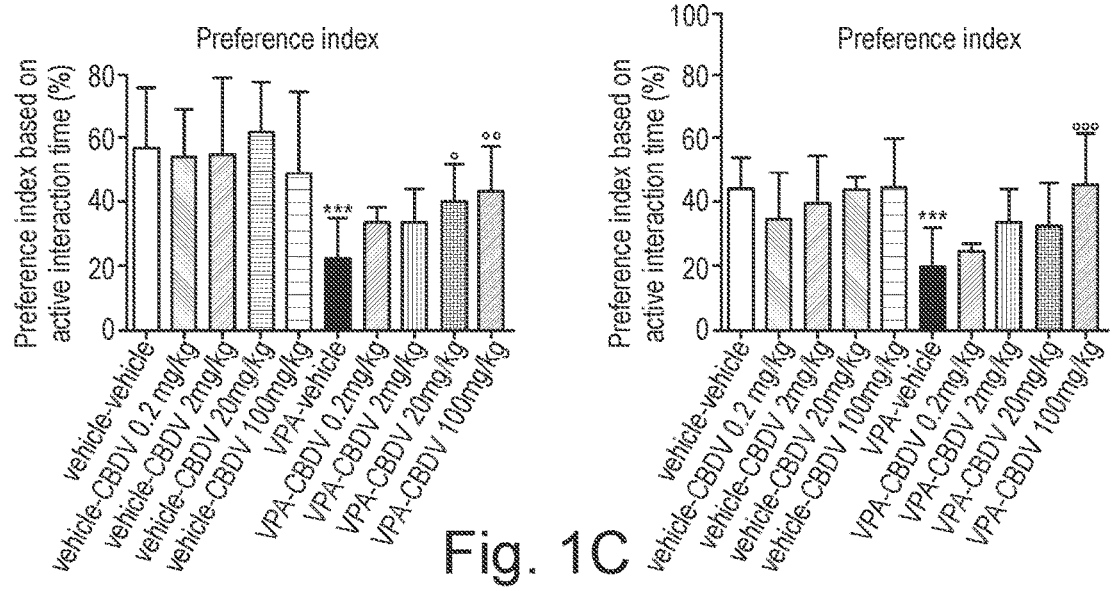
Figure 1A and 1B. The effect of CBDV on sociability and social recognition deficits in the rat VPA model of general autism Figure 2A and 2B. The effect of CBDV on repetitive behaviour and hyperactivity in the rat VPA model of general autism Figure 2C and 2D. The effect of CBDV on cognitive deficits and inflammatory biomarkers in the rat VPA model of general autism Figure 3. The effect of CBDV on discrimination index after acute and chronic treatment in the mouse model of fragile X syndrome
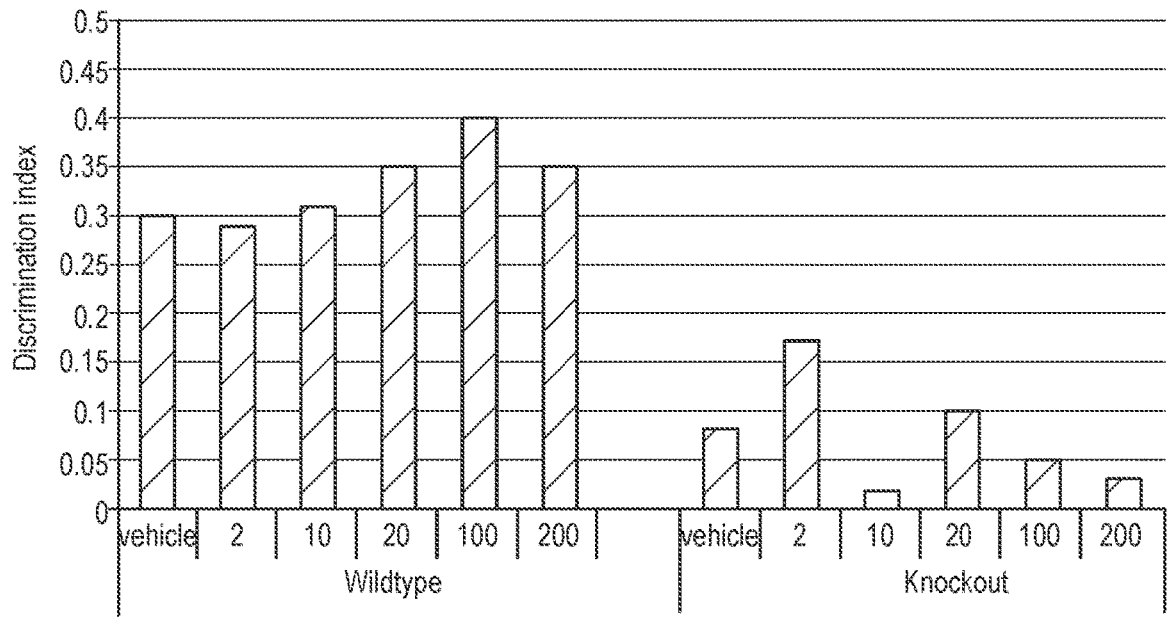
Figure 3A - acute treatment
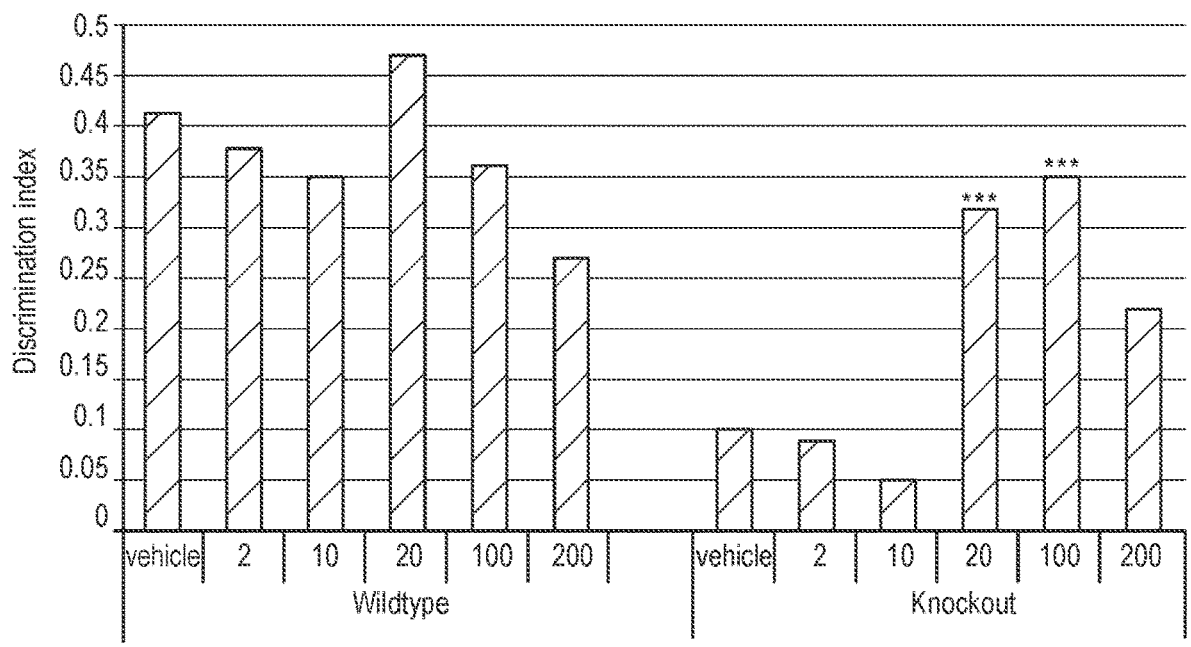
Figure 3B - chronic treatment Figure 6A-D: Effect of CBDV on symptoms in a mouse model of Rett syndrome Figure 7A-B: Effect of CBDV on symptoms in a mouse model of Rett syndrome Figure 11: Effect of CBDV on clasping duration in a mouse model of Angelman syndrome Figure 12: Effect of CBDV in the rotarod test in a mouse model of Angelman syndrome Figure 13: Effect of CBDV in the novel object recognition test in a mouse model of Angelman syndrome Figure 15: Effect of CBDV on audiogenic induced seizures in a mouse model of Angelman syndrome Figure 16: Effect of CBDV in the novel object recognition test in a rat model of schizophrenia Left hand column (blue) depicts the time in seconds spent investigating one object, the right hand column (red) shows the time spent investigating a second object. In Trial 1 the objects are identical and in Trial 2 the right hand column is a novel, unfamiliar object Figure 17: Effect of CBDV on the discrimination index in the novel object recognition test in a rat model of schizophrenia Figure 18: Effect of CBDV on social interaction test in a rat model of schizophrenia
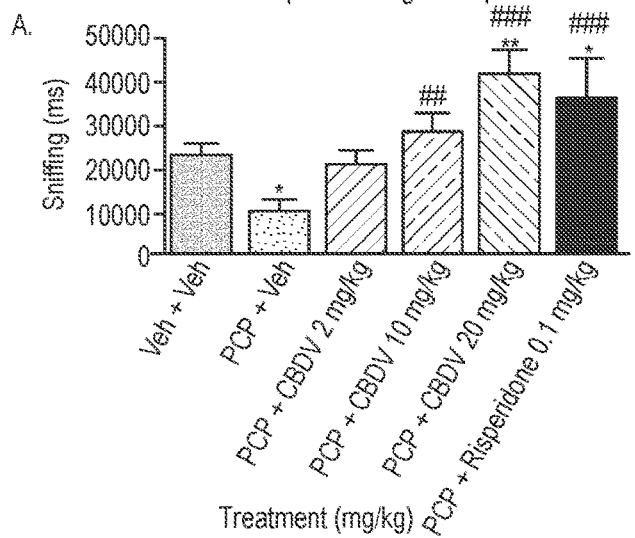
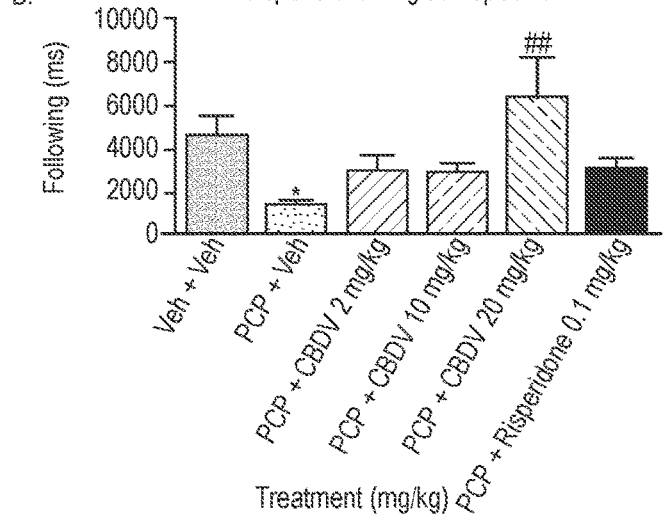
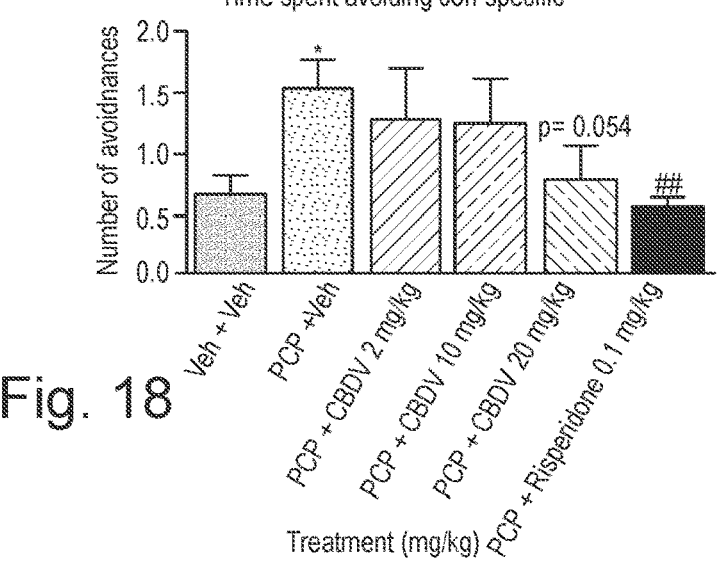
Fig. 18

USE OF CANNABIDIVARIN IN THE TREATMENT OF AUTISM SPECTRUM DISORDER, ASSOCIATED DISORDERS AND SCHIZOPHRENIA

This application is a National Stage Application of International Application No. PCT/GB2017/051007, filed on Apr. 11, 2017, which claims the benefit of priority of British Patent Application No. GB 1606098.0, filed on Apr. 11, 2016. The contents of these applications are each incorporated herein by reference.

FIELD OF THE INVENTION

The present invention relates to the use of cannabidivarin (CBDV) in the treatment of autism spectrum disorder (ASD) and ASD-associated disorders such as Fragile X syndrome (FXS); Rett syndrome (RS); or Angelman syndrome (AS). In a further embodiment the invention relates to the use of CBDV in the treatment of schizophrenia.

CBDV has been shown to be particularly effective in improving cognitive dysfunction in rodent models of ASD, FXS, RS, AS and schizophrenia.

The CBDV is preferably substantially pure. It may take the form of a highly purified extract of *cannabis* such that the CBDV is present at greater than 95% of the total extract (w/w) and the other components of the extract are characterised. Alternatively, the CBDV is synthetically produced.

Alternatively the CBDV may be used as a botanical drug substance (BDS) from a *cannabis* plant in which CBDV is the predominant cannabinoid. The CBDV may also be present in combination with other cannabinoids and non-cannabinoid components such as terpenes.

In yet a further embodiment the CBDV may be present with one or more other cannabinoids such as CBD and/or CBDA in defined ratios in which the CBDV is the predominant cannabinoid.

In use the CBDV may be used concomitantly with one or more other medicaments. The CBDV may be formulated for administration separately, sequentially or simultaneously with one or more medicaments or the combination may be provided in a single dosage form. Where the CBDV is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Autism spectrum disorder (ASD) is a condition that presents in children usually before three years of age and is characterized by a lack of social interaction, communication, interests and problems with behaviour.

The condition is relatively common as it is estimated that 1 in 100 children have some form of ASD. The condition is more prevalent in boys than girls.

In children under four the signs and symptoms of ASD include those in the area of spoken language such as delayed speech development (for example, speaking less than 50 different words by the age of two), or not speaking at all; frequent repetition of set words and phrases; speech that sounds very monotonous or flat and preferring to communicate using single words, despite being able to speak in sentences.

When responding to others these younger children will often not respond to their name being called, despite having normal hearing; reject cuddles initiated by a parent; react unusually negatively when asked to do something by someone else.

When interacting with others younger children show signs of not being aware of other people's personal space, or being unusually intolerant of people entering their own personal space; little interest in interacting with other people, including children of a similar age; not enjoying situations that most children of their age like, such as birthday parties; preferring to play alone, rather than asking others to play with them; rarely using gestures or facial expressions when communicating; and avoiding eye contact.

Symptoms involving behaviour in pre-school children include: having repetitive movements, such as flapping their hands, rocking back and forth, or flicking their fingers; playing with toys in a repetitive and unimaginative way, such as lining blocks up in order of size or colour, rather than using them to build something; preferring to have a familiar routine and getting very upset if there are changes to this routine; having a strong like or dislike of certain foods based on the texture or colour of the food as much as the taste; and unusual sensory interests for example, children with ASD may sniff toys, objects or people inappropriately.

In older school age children some of the signs and symptoms of ASD are similar to those experienced by younger children and also include other symptoms. With spoken language an older child with ASD often prefers to avoid using spoken language; has speech that sounds very monotonous or flat; may speak in pre-learned phrases, rather than putting together individual words to form new sentences; may seem to talk "at" people, rather than sharing a two-way conversation.

When responding to others, school age children with ASD often take people's speech literally and are unable to understand sarcasm, metaphors or figures of speech they may also react unusually negatively when asked to do something by someone else.

When interacting with others school age children with ASD may not be aware of other people's personal space, or are unusually intolerant of people entering their own personal space; show little interest in interacting with other people, including children of a similar age, or have few close friends, despite attempts to form friendships; not understand how people normally interact socially, such as greeting people or wishing them farewell; are unable to adapt the tone and content of their speech to different social situations for example, speaking very formally at a party and then speaking to total strangers in a familiar way; not enjoy situations and activities that most children of their age enjoy; rarely use gestures or facial expressions when communicating; and avoid eye contact.

With respect to the problems with behaviour that older children with ASD experience these include repetitive movements, such as flapping their hands, rocking back and forth, or flicking their fingers; playing in a repetitive and unimaginative way, often preferring to play with objects rather than people; developing a highly specific interest in a particular subject or activity; preferring to have a familiar routine and getting very upset if there are changes to their normal routine; having a strong like or dislike of certain foods based on the texture or colour of the food as much as the taste; unusual sensory interests for example, children with ASD may sniff toys, objects or people inappropriately.

According to DSM-IV autism is diagnosed with three core characteristics using the following criteria: A total of six (or more) items from lists (1), (2), and (3), with at least two items from list (1), and one item from each of lists (2) and (3).

List (1) qualitative impairment in social interaction, as manifested by at least two of the following:
a. marked impairment in the use of multiple nonverbal behaviours, such as eye-to-eye gaze, facial expression, body postures, and gestures to regulate social interaction;
b. failure to develop peer relationships appropriate to developmental level;
c. a lack of spontaneous seeking to share enjoyment, interests, or achievements with other people (e.g., by a lack of showing, bringing, or pointing out objects of interest); and
d. lack of social or emotional reciprocity.

List (2) qualitative impairments in communication, as manifested by at least one of the following:
a. delay in, or total lack of, the development of spoken language (not accompanied by an attempt to compensate through alternative modes of communication such as gesture or mime);
b. in individuals with adequate speech, marked impairment in the ability to initiate or sustain a conversation with others;
c. stereotyped and repetitive use of language or idiosyncratic language; and
d. lack of varied, spontaneous make-believe play or social imitative play appropriate to developmental level.

List (3) restricted, repetitive, and stereotyped patterns of behaviour, interests, and activities as manifested by at least one of the following:
a. encompassing preoccupation with one or more stereotyped and restricted patterns of interest that is abnormal either in intensity or focus;
b. apparently inflexible adherence to specific, non-functional routines or rituals;
c. stereotyped and repetitive motor mannerisms (e.g., hand or finger flapping or twisting or complex whole-body movements); and
d. persistent preoccupation with parts of objects.

According to DSM-V which was published in May 2013, the new diagnostic criteria for autism spectrum disorder is that the patient must either currently, or by history, meet criteria from A, B, C, and D as set out below.
A. Persistent deficits in social communication and social interaction across contexts, not accounted for by general developmental delays, and manifest by all 3 of the following:
  1. Deficits in social-emotional reciprocity; which may range for example from abnormal social approach and failure of normal back and forth conversation, to reduced sharing of interest, emotions, or affect, to failure to initiate or respond;
  2. Deficits in communicative behaviours used for social interaction; ranging for example, from poorly integrated verbal and non-verbal communication, to abnormalities in eye contact and body language or deficits in understanding and use of gestures, to a total lack of facial expressions and non-verbalisation; and
  3. Deficits in developing, maintaining and understanding relationships, ranging for example from difficulties adjusting behaviour to suit various social contexts, difficulties in sharing imaginative play or in making friends, to absence of interest in peers.
B. Restricted, repetitive patterns of behaviour, interests, or activities as manifested by at least two of the following:
  1. Stereotyped or repetitive motor movements, use of objects, or speech, (such as simple motor stereotypies, lining up toys or flipping plates, echolalia, idiosyncratic phrases);
  2. Insistence on sameness, inflexible adherence to routines, or ritualized patterns of verbal or non-verbal behaviour (such as extreme distress at small changes, difficulties with transitions, rigid thinking patterns, greeting rituals, need to take same route or eat same food every day);
  3. Highly restricted, fixated interests that are abnormal in intensity or focus (such as strong attachment to or preoccupation with unusual objects, excessively circumscribed or perseverative interests); and
  4. Hyper- or hypo-reactivity to sensory input or unusual interest in sensory aspects of the environment (such as apparent indifference to pain/temperature, adverse response to specific sounds or textures, excessive smelling or touching of objects, visual fascination with lights or movement).
C. Symptoms must be present in early childhood but may not become fully manifest until social demands exceed limited capacities.
D. Symptoms together limit and impair everyday functioning.

In certain genetic syndromes there is a strong prevalence of ASD or characteristics of ASD. Such syndromes can be said to be ASD-associated disorders. Such genetic syndromes include: Tuberous Sclerosis Complex, Fragile X syndrome, Cornelia de Lange syndrome, Down syndrome, Angelman syndrome, Coffin-Lowry syndrome, Cohen Laurence-Moon-Biedel syndrome, Marinesco-Sjogren syndrome, Moebius syndrome, Phelan-McDermid syndrome, CDKL5, Dup15q, Potocki-Lupski syndrome, Smith Lemli Optiz syndrome, Timothy syndrome, Prader-Willi syndrome, Rett syndrome and Williams syndrome.

It has been suggested that the genes underlying those syndromes in which ASD characteristics are very common, lead to common differences at the biological and neurological level, which in turn give rise to the presentation of ASD characteristics.

Fragile X syndrome (FXS) co-occurs with autism in many cases and is the most common cause of inherited learning disability, occurring in 1 in 3,600 males and 1 in 8,000 females. FXS is caused by the presence of an apparently unstable or 'fragile' site located on the FMR1 gene on the X chromosome. The instability is caused by an excess of genetic code in this region. Males with FXS typically show mild to severe learning disability while females with FXS usually have a mild learning disability.

Recent studies of individuals with FXS show a fairly consistent pattern of association with ASD. The percentage of individuals with FXS showing ASD characteristics or meeting ASD criteria is up to 50%. Severe ASD is relatively rare in FXS and a milder presentation of ASD-like features is more characteristic.

Impairments in social interaction in FXS are characterised by social anxiety, extreme shyness and eye gaze avoidance. These characteristics are also observed in individuals with ASD. The social impairments associated with FXS often increase as the patient gets older.

The major symptom of FXS is intellectual disability with an average IQ of 40 in males who have complete silencing of the FMR1 gene. The main difficulties in individuals with FXS are with working and short-term memory, executive function, visual memory, visual-spatial relationships, and mathematics, with verbal abilities being relatively spared.

FXS sufferers also present with prominent characteristics which may include an elongated face, large or protruding ears, flat feet, larger testes (macro-orchidism), and low muscle tone.

FXS patients also suffer from recurrent middle ear infection and sinusitis. Speech may be cluttered or nervous. Behavioural characteristics may include stereotypic movements such as hand-flapping and atypical social development, particularly shyness, limited eye contact, memory problems, and difficulty with face encoding. These features mean that individuals with FXS also meet the diagnostic criteria for autism. Genetic mouse models of FXS have also been shown to have autistic-like behaviours.

Attention deficit hyperactivity disorder (ADHD) is found in the majority of males with FXS and 30% of females, making it the most common psychiatric diagnosis in those with FXS. Hyperactivity and disruptive behaviour peak in the preschool years and then gradually decline with age, although inattentive symptoms are generally lifelong.

From their 40s onward, males with FXS begin developing progressively more severe problems in performing tasks that require the central executive of working memory.

There is currently no drug treatment that has shown benefit specifically for FXS. However, medications are commonly used to treat symptoms of attention deficit and hyperactivity, anxiety, and aggression.

Rett syndrome (RS) is a neurological disorder that is caused by a mutation on the X chromosome. RS predominantly affects females and occurs in 1 in 15,000 to 22,800 live female births. Typically, development appears to be normal in the first six to eighteen months but this is followed by a period of regression resulting in a loss of language and motor skills, leading to severe or profound learning and physical disabilities.

Autistic-like behaviours were noted in the very first description of RS in 1966. Studies have since estimated that 25% to 40% of individuals with RS show ASD-like characteristics. ASD is the most common misdiagnosis in children with RS, with many individuals being diagnosed with ASD prior to receiving a diagnosis of RS.

RS is caused by a mutation in the MECP2 gene which is found on the X chromosome. The MECP2 gene codes for the MeCP2 protein which is essential for brain development. Without this protein nerve cells in the brain are prevented from developing properly.

The symptoms associated with RS usually go unnoticed for the first few months of a child's life. The symptoms then tend to progress over several stages as outlined below.

Stage one consists of early signs and slow development, these usually appear in the first six to twelve months of the child's life. The symptoms include: a general slowness in development; hypertonia; difficulty feeding; abnormal hand movements; lack of interest in toys; and poor coordination of trunk and limbs.

Stage two is known as the regression or rapid destruction stage. This stage usually begins between the age of one and four and may last for weeks or months. The child will develop severe cognitive impairment. Problems arise with communication, language, learning, co-ordination and brain functions. Signs at this stage include: repetitive and uncontrollable hand movements; periods of distress, irritability and screaming; social withdrawal; unsteadiness when walking; rapid or slow breathing; problems sleeping; small head size; difficulty eating and gastrointestinal problems.

Many children with RS also start to suffer from epileptic seizures at this stage; up to 80% of children with the syndrome suffer from epilepsy at some stage of their illness.

Stage three is known as the plateau stage and usually begins between the ages of two and ten. This stage can last for years indeed many RS sufferers will remain in this stage for the majority of their life. The prominent symptoms include: floppiness of limbs and inability to move around; inability to use hands to hold, carry or manipulate objects; repetitive hand movements; teeth grinding; abnormal tongue movements; and lack of gain in bodyweight.

The final stage is characterized by deterioration in movement. This stage can again last for years or even decades. The main problems are caused by scoliosis of the spine; spasticity and loss of the ability to walk.

The lifespan of a child born with RS is generally shortened often due to life threatening seizures or arrhythmias.

There is no cure for RS however anti-epileptic medications are often prescribed to control the seizures along with a high calorie diet and physiotherapy to help control the symptoms.

Angelman syndrome (AS) occurs in approximately 1 in 12,000 to 15,000 individuals and is caused by abnormalities on chromosome 15. Individuals with AS typically show severe to profound learning disability, significant difficulties with mobility and communication in addition to seizures.

It has been suggested that between 50% and 80% of individuals with AS meet the criteria for ASD.

Typical characteristics of Angelman syndrome include: delayed development which is usually noticeable from 6-12 months of age; severe language impairment with little or no speech; movement and balance problems (ataxia); frequent seizures (epilepsy) in around 85% of cases; a small head size (microcephaly); sociable behaviour with frequent smiling.

A genetic anomaly responsible for AS which occurs by chance around the time of conception. The UBE3A gene is either absent or malfunctions. A child usually inherits one copy of the UBE3A gene from each parent. Both copies are switched on (active) in most of the body's tissues. However, in certain areas of the brain, only the gene inherited from the mother is active. In most cases of AS (about 70%), the child's maternal copy of the UBE3A gene is missing, which means there's no active copy of the UBE3A gene in the child's brain.

Schizophrenia is a psychiatric diagnosis that describes a mental illness characterised by impairments in the perception or expression of reality, most commonly manifesting as auditory hallucinations, paranoid or bizarre delusions or disorganised speech and thinking in the context of significant social, occupational or cognitive dysfunction.

Schizophrenia is often described in terms of positive and negative symptoms. Positive symptoms include delusions, auditory hallucinations, and thought disorder, and are typically regarded as manifestations of psychosis. Negative symptoms are so-named because they are considered to be the loss or absence of normal traits or abilities, and include features such as flat or blunted affect and emotion, poverty of speech (alogia), anhedonia, and lack of motivation (avolition). A third symptom grouping, the disorganisation syndrome, includes chaotic speech, thought, and behaviour. The disorder is also thought to affect cognition, which also usually contributes to chronic problems with behaviour and emotion.

Cognitive symptoms are often detected when neuropsychological tests are performed on schizophrenia patients. They include the following: poor "executive functioning" (the ability to absorb and interpret information and make decisions based on that information); inability to sustain attention; and problems with "working memory" (the ability to keep recently learned information in mind and use it right away). Such cognitive dysfunction often interferes with the patient's ability to lead a normal life and earn a living. They can cause great emotional distress.

Treatment for the positive symptoms of schizophrenia is usually with antipsychotic medications; however the negative and cognitive symptoms remain largely untreated.

Testing compounds for their effectiveness on signs and symptoms of ASD, ASD-associated disorders and schizophrenia is challenging given that these disorders have so many different affected symptom domains.

The rodent valproic acid model is a widely accepted model of ASD. Rat foetuses are exposed to valproic acid on the 12.5th day of gestation to produce VPA rats. The VPA rats present behavioural aberrations observed in autism such as delayed maturation, lower body weight, delayed motor development, and attenuated integration of a coordinated series of reflexes, delayed nest-seeking response mediated by olfactory system, and normal negative geotaxis.

Additionally there are particular animal models which can be used to test particular syndromes which present with ASD like characteristics such as FXS, RS and AS or ASD-associated disorders.

Male patients with FXS lack the FMR1 protein due to silencing of the FMR1 gene by amplification of a CGG repeat and subsequent methylation of the promoter region. A knockout model for FXS in mice is a well-known model used to test compounds for their effectiveness in the treatment of FXS. Mice lack normal FMR1 protein and show macro-orchidism, learning deficits, and hyperactivity.

The MeCP2 knockout mouse model is able to evaluate the effectiveness of a treatment the symptoms that present in RS. Mice lacking the MeCP2 gene show severe neurological symptoms at approximately six weeks of age. After several months, heterozygous female mice also show autism like behavioural symptoms.

The UBE3A mouse model is used to evaluate a compounds effectiveness in the treatment of AS. This model has been shown to recapitulate many of the phenotypic features of AS, including motor dysfunction, increased seizure susceptibility, and hippocampal-dependent learning and memory deficits in mice with the knockout gene.

The phencyclidine (PCP) model is used to evaluate the effectiveness of a compound on cognitive dysfunction in schizophrenia. PCP is a non-competitive N-methyl-D-aspartate (NMDA) receptor antagonist, and reproduces a schizophrenia-like psychosis including positive symptoms, negative symptoms and cognitive dysfunction. PCP-treated animals exhibit hyper-locomotion as an index of positive symptoms, and a social behavioural deficit in a social interaction test and enhanced immobility in a forced swimming test as indices of negative symptoms. They also show a sensorimotor gating deficit and cognitive dysfunctions in several learning and memory tests such as the Novel Object Recognition (NOR) test.

The NOR test is used to evaluate cognition, particularly recognition memory, in rodent models of CNS disorders, such as ASD, ASD-associated disorders and schizophrenia. The test is based on the tendency of rodents to spend more time exploring a novel object than a familiar one. The choice to explore the novel object reflects the use of learning and recognition memory.

The NOR test is conducted in an open field arena with two different kinds of objects. Both objects are generally consistent in height and volume, but are different in shape and appearance. During habituation, the animals are allowed to explore an empty arena. Twenty-four hours after habituation, the animals are exposed to the familiar arena with two identical objects placed at an equal distance. The next day, the mice are allowed to explore the open field in the presence of the familiar object and a novel object to test short-term and long-term recognition memory. The time spent exploring each object and the discrimination index percentage is recorded. This test is useful for assessing cognitive dysfunction in rodent models of ASD, FXS, RS, AS and schizophrenia.

The Food and Drug Administration (FDA) has approved two drugs for treating irritability associated with the autism (risperidone and aripiprazole) which are both antipsychotic medications. However, there are currently no approved medications for treating autism's core characteristics. Antipsychotics can ease core symptoms to some extent, for example relieving irritability often improves sociability, reduces tantrums, aggressive outbursts and self-injurious behaviour. The disadvantages associated with antipsychotics are that this class of medicaments is known to have side effects including severe weight gain, stiffness and shakiness. Accordingly it would be desirable to provide a more effective medication able to treat the core characteristics of ASD and offer an improved side effect profile.

The endocannabinoid system has been linked to physiological progression of autism spectrum disorders, possibly implicating CB1 and CB2 receptors.

The phytocannabinoids are known to interact with the endocannabinoid system.

The phytocannabinoid tetrahydrocannabinol (THC) in the form of dronabinol, a CB1 agonist, has been used to treat an autistic child (Kurz and Blass, 2010). Problems associated with the use of CB1 agonists are psychoactivity, anxiety and hallucinations.

Patent applications GB 2,492,487 and GB 2,434,312 describe the use of cannabinoids in the treatment of neurodegenerative diseases and disorders. Furthermore patent application WO 2006/017892 describes the use of CBD in the treatment of schizophrenia.

Patent application WO 2014/146699 describes the use of CB1 receptor antagonists in the treatment of diseases associated with dendritic abnormalities. Such diseases include AS and RS. The application is exemplified by the use of rimonabant in the FMR1 knockout mouse model which is a model of FXS.

The CB1 antagonist, rimonabant, has been shown to have serious side effects such as suicide ideation which limit its use.

The present application relates to the use of a phytocannabinoid which is neither a CB1 agonist nor antagonist. Cannabidivarin (CBDV) is known to have a low affinity for the CB1 receptor. Hill et al. (2013) demonstrated that a plant extract comprising CBDV showed greater affinity for CB1 cannabinoid receptors than purified CBDV in both MF1 mouse brain and hCB1-CHO cell membranes; however neither bound with high enough affinity to be described as an agonist or antagonist.

CBDV has been shown to be effective in animal models of seizure (Hill et al., 2012) and WO 2011/121351.

To date there are no studies of the use of CBDV in the treatment of ASD or ASD-associated disorders such as FXS, RS and AS or schizophrenia. Such symptoms as described above are difficult to treat, therefore many patients with ASD or ASD-associated disorders such as FXS, RS and AS and schizophrenia have unmet needs with respect to the treatment of their disease.

BRIEF SUMMARY OF THE DISCLOSURE

In accordance with a first aspect of the present invention there is provided Cannabidivarin (CBDV) for use in the treatment of one or more symptoms or disease characteristics associated with autistic spectrum disorder (ASD) or ASD-associated disorders, as defined by DSM-IV, wherein the symptoms or disease characteristic is one or more selected from the group consisting of: (i) qualitative impairment in social interaction; (ii) qualitative impairment in communication; and (iii) restricted repetitive and stereotyped patterns of behaviour interest and activities.

Preferably the symptoms or disease characteristics of qualitative impairment in social interaction include one or more of: (a) marked impairment in the use of multiple nonverbal behaviours, such as eye-to-eye gaze, facial expression, body postures, and gestures to regulate social interaction; (b) failure to develop peer relationships appropriate to developmental level; (c) a lack of spontaneous seeking to share enjoyment, interests, or achievements with other people (e.g., by a lack of showing, bringing, or pointing out objects of interest); and (d) lack of social or emotional reciprocity.

Preferably the symptoms or disease characteristics of qualitative impairment in communication include one or more of: (a) delay in, or total lack of, the development of spoken language (not accompanied by an attempt to compensate through alternative modes of communication such as gesture or mime); (b) in individuals with adequate speech, marked impairment in the ability to initiate or sustain a conversation with others; (c) stereotyped and repetitive use of language or idiosyncratic language; and (d) lack of varied, spontaneous make-believe play or social imitative play appropriate to developmental level.

Preferably the symptoms or disease characteristics of restricted repetitive and stereotyped patterns of behaviour interest and activities include one or more of: (a) encompassing preoccupation with one or more stereotyped and restricted patterns of interest that is abnormal either in intensity or focus; (b) apparently inflexible adherence to specific, non-functional routines or rituals; (c) stereotyped and repetitive motor mannerisms (e.g., hand or finger flapping or twisting or complex whole-body movements); and (d) persistent preoccupation with parts of objects.

Preferably the symptoms or characteristics associated with of autistic spectrum disorder comprise at least two symptoms associated with qualitative impairment in social interaction; at least one symptom associated with qualitative impairment in communication and at least one symptom associated with restricted repetitive and stereotyped patterns of behaviour interest and activities.

In accordance with a second aspect of the present invention there is provided Cannabidivarin (CBDV) for use in the treatment of autistic spectrum disorder (ASD) or ASD-associated disorders as defined by DSM-V, wherein the symptoms or disease characteristic is one or more selected from the group consisting of: (a) persistent deficits in social communication and social interaction across contexts, not accounted for by general developmental delays, and (b) restricted, repetitive patterns of behaviour, interests, or activities.

Preferably the symptoms or disease characteristics of (a) persistent deficits in social communication and social interaction across contexts, not accounted for by general developmental delays include one or more of: (i) deficits in social-emotional reciprocity; (ii) deficits in nonverbal communicative behaviours used for social interaction; and (iii) deficits in developing and maintaining relationships.

Preferably the symptoms or disease characteristics of (b) restricted, repetitive patterns of behaviour, interests, or activities include one or more of: (i) stereotyped or repetitive speech, motor movements, or use of objects; excessive adherence to routines, (ii) ritualized patterns of verbal or nonverbal behaviour, or excessive resistance to change; (iii) highly restricted, fixated interests that are abnormal in intensity or focus; and (iv) hyper- or hypo-reactivity to sensory input or unusual interest in sensory aspects of environment.

Preferably the symptoms or disease characteristics associated with of autistic spectrum disorder comprise all three symptoms associated with (a) persistent deficits in social communication and social interaction across contexts, not accounted for by general developmental delays together with at least two of (b) restricted, repetitive patterns of behaviour, interests, or activities.

In this aspect, treatment of ASD and ASD-associated disorders encompass the treatment of the condition as a whole as opposed to the individual symptoms. Accordingly the present invention does not encompass CBDV for use in the treatment of seizures.

Preferably the ASD-associated disorder is taken from the group: Fragile X syndrome; Rett syndrome; or Angelman syndrome.

In accordance with a third aspect of the present invention there is provided Cannabidivarin (CBDV) for use in the treatment of schizophrenia.

Preferably the CBDV is for use in the treatment of positive or negative symptoms associated with schizophrenia. In particular the CBDV is particularly useful in the treatment of the negative symptoms associated with social withdrawal.

In accordance with a fourth aspect of the present invention there is provided Cannabidivarin (CBDV) for use in the treatment of cognitive dysfunction.

Preferably the cognitive dysfunction occurs in patients with ASD, ASD-associated disorders or schizophrenia.

In one embodiment treatment of the cognitive dysfunction is associated with the treatment of memory. Preferably the treatment is of short term memory and/or long term memory.

In a further embodiment the CBDV is for use in combination with one or more concomitant medicaments which may be taken by the patient to treat the condition and/or one or more symptoms associated therewith. Such as, for example, melatonin for sleeping problems, SSRI for depression, anticonvulsants for epilepsy, methylphenidate for ADHD or antipsychotics for aggression or self-harming behaviour. In this respect the CBDV of the present invention is not used to treat seizures.

Preferably the one or more concomitant medicament is an anti-epileptic drug (AED). The AED may be the cannabinoid CBD and as such a combination of CBDV and CBD may be used.

In a further embodiment the CBDV is substantially pure. The CBDV may be present as a highly purified extract of *cannabis* which comprises at least 95% (w/w) CBDV. Preferably the extract comprises less than 0.15% THC.

In an alternative embodiment the CBDV is present as a synthetic compound.

Alternatively the CBDV may be used as a botanical drug substance (BDS) from a *cannabis* plant in which CBDV is the predominant cannabinoid. The CBDV may also be present in combination with other cannabinoids and non-cannabinoid components such as terpenes.

In yet a further embodiment the CBDV may be present with one or more other cannabinoids such as CBD and/or CBDA in defined ratios in which the CBDV is the predominant cannabinoid. Determining an effective dose in humans will depend on, for example the mode of delivery (i.v. or oral), the formulation and the bioavailability of the CBDV when delivered and might range between 0.01 and 100 mg/kg/day. Furthermore the fact that cannabinoids often show bell-shaped dose response curves makes determining a dose of CBDV more difficult.

Preferably the dose of CBDV is greater than 0.01 mg/kg/day. Thus for a 15 kg patient a dose of greater than 0.15 mg of CBDV per day would be provided. Doses greater than 0.1 mg/kg/day, such as greater than 1 mg/kg/day, such as greater than 5 mg/kg/day, greater than 10 mg/kg/day, greater than 15 mg/kg/day and greater than 20 mg/kg/day are also envisaged to be effective.

In use the CBDV may be effective in a therapeutic amount of between 1 to 30 mg/kg/day and it may also be administered as an oral formulation.

Preferably the CBDV is provided over an extended period; more preferably this period is at least seven days.

In a further embodiment the CBDV may be used as a dietary supplement or food additive in order to improve symptoms in ASD, ASD-associated conditions or schizophrenia.

In accordance with a fifth aspect of the present invention there is provided a method of treating one or more symptoms or disease characteristics associated with autistic spectrum disorder (ASD) or ASD-associated disorders in a subject, as defined by DSM-IV, wherein the symptoms or disease characteristic is one or more selected from the group consisting of: qualitative impairment in social interaction; qualitative impairment in communication; and restricted repetitive and stereotyped patterns of behaviour interest and activities, comprising administering an effective amount of cannabidivarin (CBDV) to the subject in need thereof. Preferably the subject is a human.

In accordance with a sixth aspect of the present invention there is provided a method of treating one or more symptoms or disease characteristics associated with autistic spectrum disorder (ASD) or ASD-associated disorders in a subject, as defined by DSM-V, wherein the symptoms or disease characteristic is one or more selected from the group consisting of: (a) persistent deficits in social communication and social interaction across contexts, not accounted for by general developmental delays, and (b) restricted, repetitive patterns of behaviour, interests, or activities, comprising administering an effective amount of cannabidivarin (CBDV) to the subject in need thereof.

Preferably the ASD-associated disorder is taken from the group: Fragile X syndrome; Rett syndrome; or Angelman syndrome.

In accordance with a seventh aspect of the present invention there is provided a method of treating schizophrenia in a subject comprising administering an effective amount of cannabidivarin (CBDV) to a subject in need thereof. Preferably the subject is a human.

In accordance with an eighth aspect of the present invention there is provided a method of treating cognitive dysfunction comprising administering cannabidivarin (CBDV) to a subject in need thereof. Preferably the subject is a human.

The human dose equivalent (HED) can be estimated using the following formula:

$$HED = \text{Animal dose (mg/kg) multipled by } \frac{\text{Animal } K_m}{\text{Human } K_m}$$

The $K_m$ for a mouse is 3, for a rat the $K_m$ is 6 and the $K_m$ for a human is 37.

Definitions

Definitions of some of the terms used to describe the invention are detailed below:

The cannabinoids described in the present application are listed below along with their standard abbreviations.

TABLE 1

Cannabinoids and their abbreviations

| | |
|---|---|
| CBD | Cannabidiol |

| | |
|---|---|
| CBDV | Cannabidivarin |

TABLE 1-continued

Cannabinoids and their abbreviations

THC    Tetrahydrocannabinol

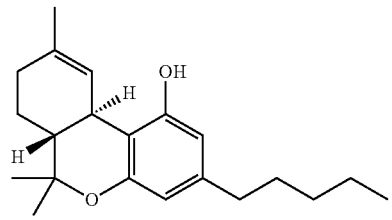 [SMILES: CCCCCc1cc(O)c2c(c1)OC(C)(C)[C@@H]1CCC(C)=C[C@@H]21]

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Substantially pure CBDV" is defined as CBDV that is greater than 95% (w/w) pure. More preferably greater than 96% (w/w) through 97% (w/w) thorough 98% (w/w) to 99% % (w/w) and greater.

"Highly purified cannabinoid extracts" are defined as cannabinoids that have been extracted from the *cannabis* plant and purified to the extent that other cannabinoids and non-cannabinoid components that are co-extracted with the cannabinoids have been substantially removed, such that the highly purified cannabinoid is greater than or equal to 95% (w/w) pure.

"Botanical drug substance" or "(BDS)" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of *cannabis*, BDS derived from *cannabis* plants do not include highly purified Pharmacopoeial grade cannabinoids. In a BDS comprising cannabinoids the cannabinoid will be present in an amount of less than 95% (w/w).

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Cognitive dysfunction" is defined as the loss of intellectual functions such as thinking, remembering, and reasoning with sufficient severity to interfere with daily functioning. Patients with cognitive dysfunction have trouble with verbal recall, basic arithmetic, and concentration.

An ASD-associated disorder is defined as genetic syndromes where there is a strong prevalence of ASD or characteristics of ASD. Such genetic syndromes include: Tuberous Sclerosis Complex, Fragile X syndrome, Cornelia de Lange syndrome, Down syndrome, Angelman syndrome, Coffin-Lowry syndrome, Cohen Laurence-Moon-Biedel syndrome, Marinesco-Sjogren syndrome, Moebius syndrome, Phelan-McDermid syndrome, CDKL5, Dup15q, Potocki-Lupski syndrome, Smith Lemli Optiz syndrome, Timothy syndrome, Prader-Willi syndrome, Rett syndrome and Williams syndrome.

A symptom or disease characteristic associated with ASD or ASD-associated disorders are defined as the diagnostic criteria as defined by either DSM-IV or DSM-V as described above (under the section "Background to the Invention").

BRIEF DESCRIPTION OF THE DRAWINGS

Embodiments of the invention are further described hereinafter with reference to the accompanying drawings, in which FIG. 1 A-C shows the effect of CBDV on sociability and social recognition deficits in the rat VPA model of general autism;

FIG. 3 A-B shows the effect of CBDV on discrimination index after acute and chronic treatment in the mouse model of fragile X syndrome;

FIG. 18** shows the effect of CBDV on social interaction in a rat model of schizophrenia.

Figure 17:
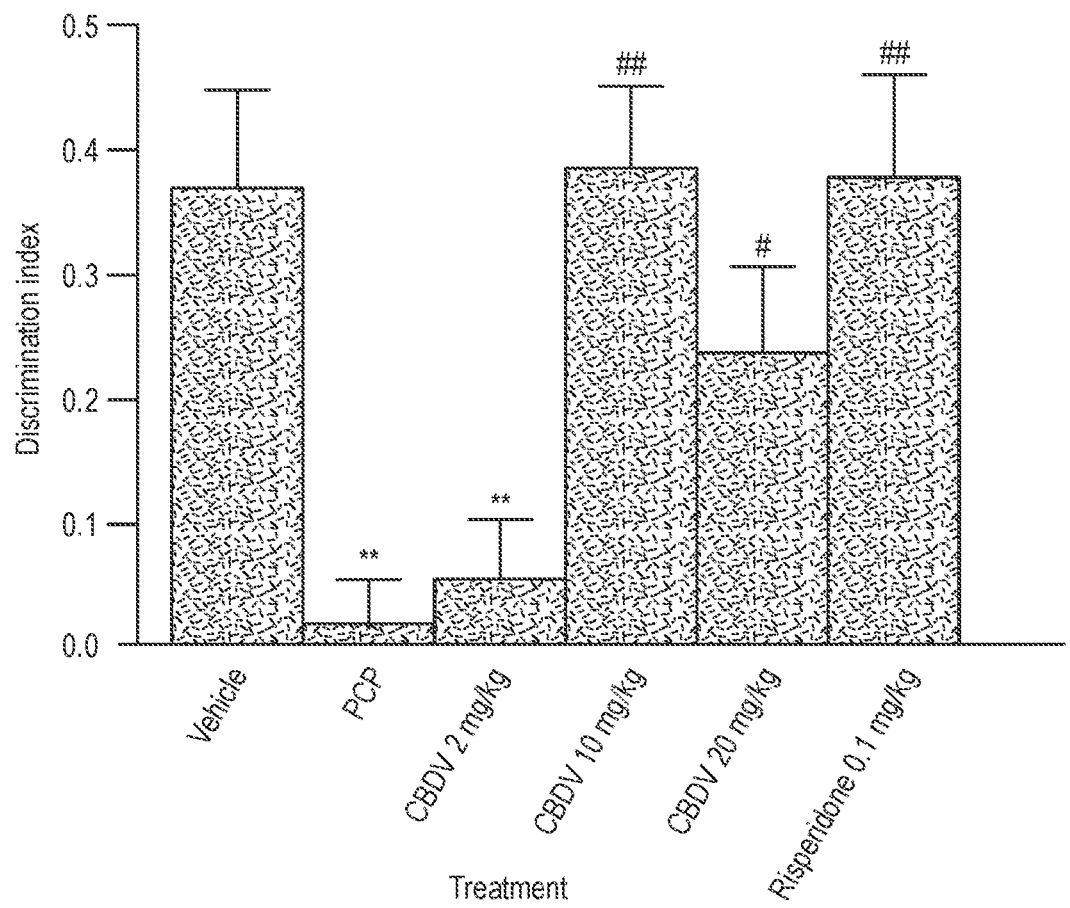
FIG. 17 shows the effect of CBDV on the discrimination index in the novel object recognition test in a rat model of schizophrenia, data is expressed as P<0.01; Significant reduction in DI compared to vehicle, #P<0.05-##P<0.01; Significant reversal of the reduction in DI compared to PCP.

For all figures, except FIG. 17, data are expressed as mean±S.E.M. *p<0.05,***p<0.001 vs WT-vehicle; ∞p<0.01, ∞∞∞p<0.001 vs KO-vehicle. Two-way ANOVA followed by Bonferroni post hoc test.

DETAILED DESCRIPTION

Example 1: Use of Cannabidivarin (Cbdv) in A Mouse Model of Autism Spectrum Disorder The phytocannabinoid cannabidivarin (CBDV) was evaluated in a rodent model of autism spectrum disorder (ASD).

In utero exposure of rodents to valproic acid (VPA) has been shown to induce a phenotype with behavioural characteristics similar to those observed in ASD and provides a robust animal model for social cognitive impairment understanding and a potential screen for the development of novel therapeutics for this condition (Foley et al. 2012).

Thus, in utero exposure to VPA has been used as a reliable model to increase the understanding of behavioural effects evaluated by specific tests as sociability, social preference and stereotypic behaviour, also observed in human patients (Schneider and Przewlocki, 2005).

Example 1 describes the use of prenatal VPA exposure in rats to evaluate the efficacy of chronic CBDV administration in reversing the autism-like behaviours present in this model.

Materials and Methods

Prenatal VPA Administration

Pregnant Sprague-Dawley rats (Charles River, Calco, Italy), received a single intraperitoneal injection of 500 mg/kg sodium valproate on the 12.5 day after conception, and control females were injected with physiological saline at the same time. Sodium valproate (Sigma Aldrich, Milan, IT) was dissolved in saline at a concentration of 250 mg/ml.

Females were housed individually and were allowed to raise their own litters. The offspring was weaned on postnatal day (PND) 21, separated by sex and the animals were kept four to a cage, with controlled temperature and light conditions. Rats had free access to food (standard laboratory pellets) and water. All the experiments were performed in the light phase between 09:00 and 15:00.

CBDV Treatment

CBDV was dissolved in ethanol, cremophor and saline (1:1:18). Symptomatic treatment with CBDV at doses of 0.2, 2, 20, and 100 mg/kg/day i.p. was performed starting from PND 34 (early adolescence) till 56 (early adulthood), both in male and female offspring of dams injected with VPA 500 mg/kg (or vehicle) on day 12.5 after conception. At PND 56, a series of behavioural tests was performed in order to assess the effect of chronic CBDV on sociability, social novelty, short-term memory, locomotion and stereotyped/repetitive behaviours.

Behavioural Studies

Locomotor activity and repetitive behaviours: Locomotor activity was recorded in an activity cage for 20 minutes with the aid of Anymaze program (Ugo Basile, Italy). In this period, repetitive behaviours (self-grooming and digging) were measured by an observer blind to the treatment group.

Sociability and preference for social novelty: These behaviours were investigated in a 3-chamber apparatus which allows for the measurement of social approach and social preference. In brief, animals were placed into a novel arena (80 cm×31.5 cm) composed of three communicating chambers separated by Perspex walls with central openings allowing access to all chambers for 5 min.

Distance moved (m) and time spent (s) in the various compartments was assessed during this time to evaluate general locomotor activity and ensure that animals did not have a preference for a particular side of the arena.

Following this acclimatisation period, animals were briefly confined to the central chamber while an unfamiliar rat confined in a small wire cage was placed in one of the outer chambers. An identical empty wire cage was placed in the other chamber. The unfamiliar rat was randomly assigned to either the right or left chamber of the arena. The test animal was then allowed to explore the arena/chambers for a further 5 min. Time spent engaging in investigatory behaviour with the rat was evaluated with the aid of Anymaze program (Ugo Basile, Italy) in order to examine social approach.

To investigate the preference for social novelty, a novel unfamiliar rat was then placed in the empty cage and the test animal was then allowed to explore the arena/chambers for a further 5 min. Time spent engaging in investigatory behaviour with the novel unfamiliar rat was evaluated with the aid of Anymaze program (Ugo Basile, Italy) in order to examine preference for social novelty.

Short-term memory: The experimental apparatus used for the object recognition test was an open-field box (43×43×32 cm) made of Plexiglas, placed in a dimly illuminated room. The experiment was performed and analysed as previously described (Zamberletti et al, 2014). Animals performed each test individually.

Each animal was placed in the arena and allowed to explore two identical previously unseen objects for 5 minutes (familiarization phase). After an inter-trial interval of 3 minutes one of the two familiar objects was replaced by a novel, previously unseen object and rats were returned to the arena for the 5-minute test phase. During the test phase the time spent exploring the familiar object (Ef) and the new object (En) was videotaped and recorded separately by two observers blind to the treatment groups and the discrimination index was calculated as follows: $[(En-Ef)/(En+Ef)] \times 100$.

Neuroinflammation Studies

At the end of the study, on PND 59, male rats treated with CBDV 20 mg/kg i.p. were sacrificed and the hippocampus was collected 24 hours after the last CBDV injection and stored at −80° C. for evaluation of changes in protein expression of components of the endocannabinoid system (CB1 and CB2 receptors, the endocannabinoid degrading enzymes, FAAH and MAGL and the synthetic enzymes, DAGLα and NAPE-PLD); neuroinflammatory markers (GFAP (astrocytic marker), Iba1 (microglial marker), CD11b (activated microglial marker), TNF-α (proinflammatory cytokine) and iNOS (inflammatory mediator)); synaptic markers (Synaptophysin (synaptic vesicle protein), PSD-95 (post synaptic density protein) and the neurotrophins, BDNF and IGF by Western blotting.

Statistical analysis: Data were expressed as mean±. Results were analysed by unpaired Student's t test or two-way ANOVA, followed up by Bonferroni's post hoc test. The level of statistical significance was set at p<0.05.

Results

FIG. 1A shows the effect of the different doses of CBDV treatment on social novelty preference in offspring of VPA- and vehicle-exposed rats, as measured through the three chamber apparatus. CBDV at 20 mg/kg was demonstrated to have a statistically significant effect (p<0.001 in males and p<0.01 in females) on restoration of social novelty preference.

During the habituation phase, no differences in the time spent in each compartment of the maze were observed, suggesting that animals did not show a preference for a particular side of the arena (data not shown).

During the sociability test, two-way ANOVA revealed significant main effects of VPA and CBDV on sociability. VPA-exposed rats spent significantly less time in the chamber containing the unfamiliar rat with respect to the time spent in the empty compartment when compared to controls. The deficit in sociability present in VPA-treated rats was confirmed by the preference index that showed a significant reduction by about 48% in the percentage of time spent exploring the unfamiliar rat with respect to the empty compartment.

FIG. 1B shows that CBDV treatment at all doses significantly reduced the impairment in sociability observed in VPA rats, the preference index being only reduced by about 13% in VPA-CBDV animals compared to controls.

FIG. 1C shows the effect of CBDV treatment on social novelty preference in offspring of VPA- and vehicle-exposed rats, as measured through the three chamber apparatus.

Control mice spent significantly more time exploring the novel rat than the known rat (p<0.01). In contrast, VPA animals spent similar time exploring the two stimuli.

Treatment with CBDV at doses of 20 mg/kg and 100 mg/kg reversed the deficit in social preference in VPA rats, as demonstrated by the fact that VPA-CBDV rats spent significantly more time exploring the novel rats with respect to the familiar one.

Figure 2A:
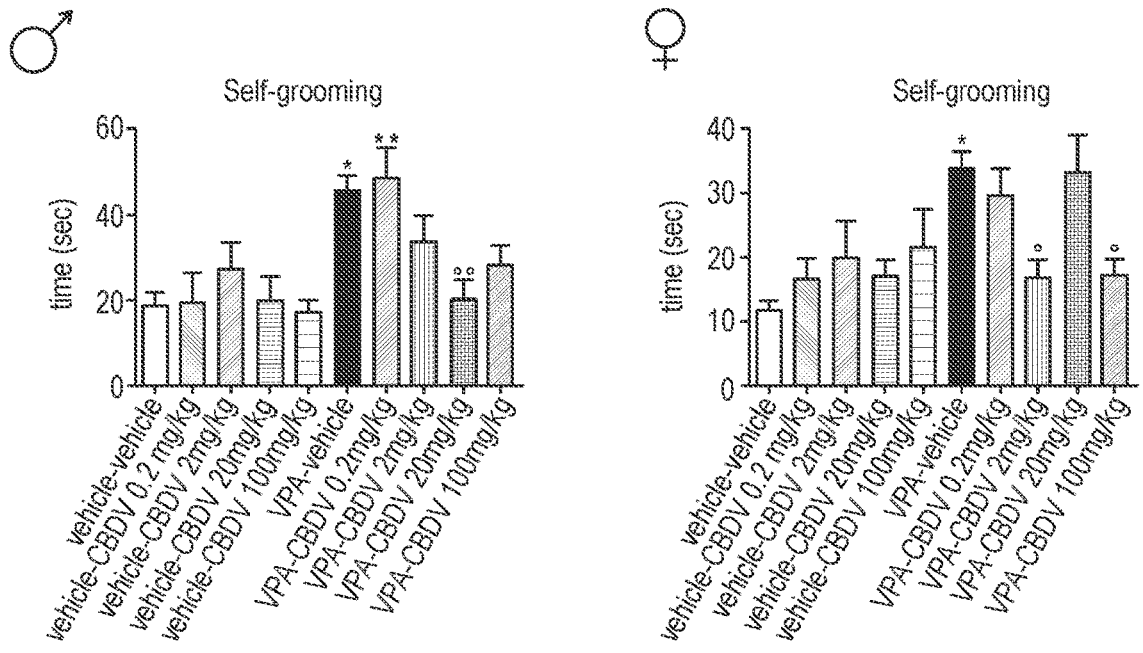
FIG. 2 A-D shows the effect of CBDV on repetitive behaviours, hyperactivity, cognitive deficits and biomarkers in the rat VPA model of general autism.

FIG. 2A shows the effect of CBDV treatment on repetitive behaviours (compulsive self-grooming), in VPA-exposed offspring. Prenatal VPA exposure significantly increased the time spent in compulsive self-grooming. CBDV administration at 20 mg/kg in males and 2 and 100 mg/kg in females was able to significantly normalize this behaviour.

Figure 2B:
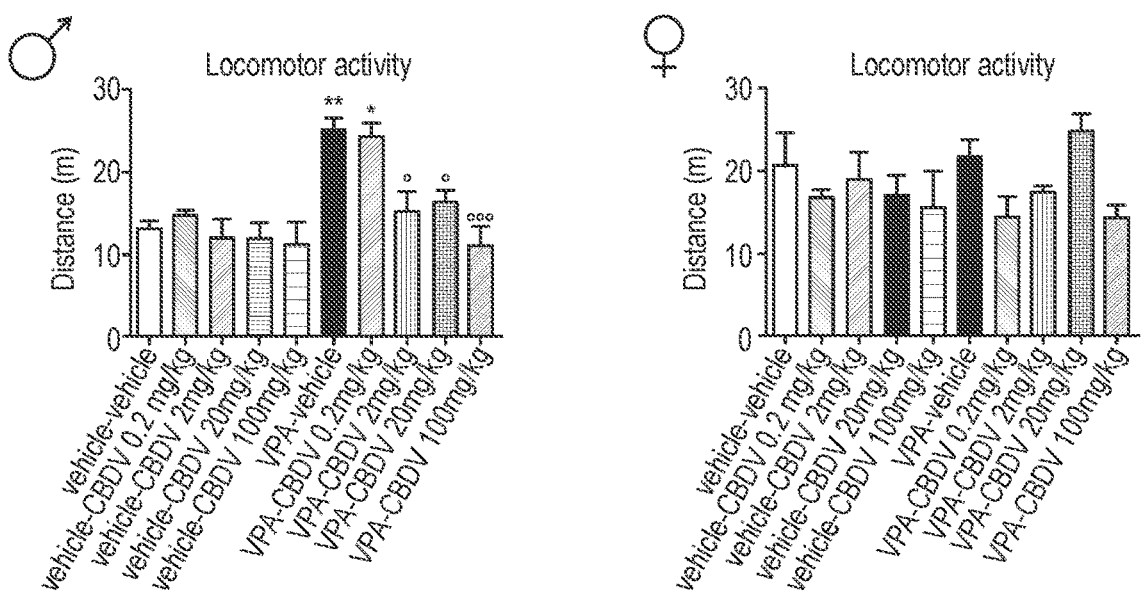

FIG. 2B shows the effect of CBDV treatment on locomotor activity in VPA offspring. VPA administration significantly increased locomotion by about 70% compared to control and CBDV administration at 2, 20 and 100 mg/kg in males was able to normalize this.

Figure 2C:
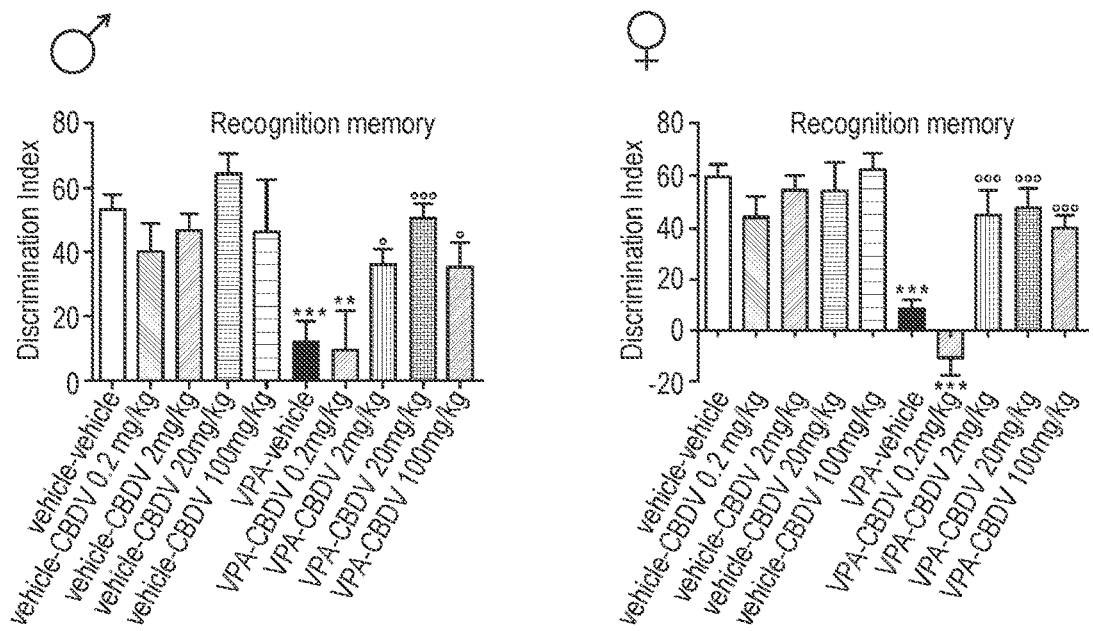

FIG. 2C shows the effect of CBDV treatment on short-term memory, evaluated through the novel object recognition test. Prenatal VPA administration significantly impaired short-term memory, as demonstrated by a significant reduction of the discrimination index by about 59% with respect to controls. CBDV at doses of 2, 20 and 100 mg/kg completely and significantly reversed the short-term memory deficit in both male and female VPA rats, without affecting per se recognition memory when administered to vehicle-treated (non VPA) rats.

Figure 2D:
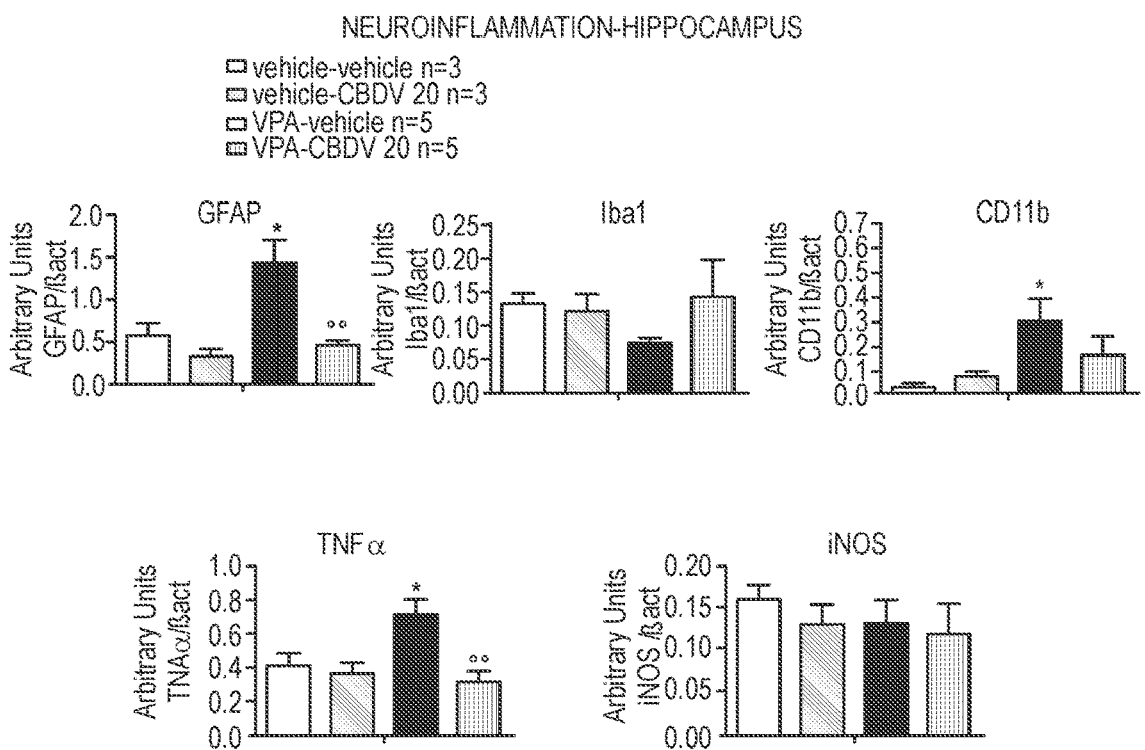

FIG. 2D shows there were significant increases in GFAP and CD11b expression in the hippocampus, paralleled by a concomitant enhancement of TNFα levels. In contrast, no changes were seen in Iba1 and iNOS levels after prenatal VPA exposure. Chronic CBDV administration completely normalised the expression of those inflammatory markers that were increased when administered to VPA-exposed rats and had no effect in control rats.

Conclusions

These data demonstrate that CBDV provided an effective treatment on the alterations in sociability, social novelty preference, short-term memory, repetitive behaviours and locomotion induced by prenatal VPA exposure offspring.

CBDV administration does not affect per se any of the behaviours that were under investigation.

These data indicate that CBDV at doses of 2, 20 and 100 mg/kg was able to reverse the autism-like phenotype in VPA-exposed rats and is therefore a potential novel treatment option for ASD.

Furthermore CBDV was able to normalise the overexpression of particular inflammatory biomarkers which were found to be increased in rats treated with VPA. These data suggest that the CBDV treatment was able to modulate the deficits that occur in autism such as cognitive and behavioural deficits at a cellular level.

Example 2: Use of Cannabidivarin (Cbdv) in A Mouse Model of Fragile X Syndrome

The phytocannabinoid cannabidivarin (CBDV) was evaluated in a mouse model of Fragile X syndrome (FXS). Such model evaluates the treatment on cognitive deficits and seizures present in Fmr1 knockout (KO) mice.

Materials and Methods

Animals

Fmr1 KO mice and wild type mice were obtained and housed four per cage in a temperature of 21° C.±1° C. and humidity of 55%±10% controlled environment. Food and water were available ad libitum. All experiments were performed during the light phase of a 12 hour light/dark cycle (08:00 to 20:00). Animals were handled for one week before the start of experiments. All behavioural tests were performed by researchers blind to the different experimental groups.

Novel Object Recognition Task

On day one mice were habituated for 10 minutes to the empty V-maze in which the task was to be performed. On the second day the mice went back to the maze for 10 minutes which contained two identical objects at the end of each corridor in the V-maze.

The following day the mice were placed again in the same maze for a further 10 minutes but one of the familiar objects was replaced for a novel object. The total time spent exploring the novel and familiar object was recorded. A discrimination index was calculated as the difference between the time spent exploring the novel and familiar object divided by the total time exploring the two objects. A high discrimination index (0.3-0.5) is considered to reflect memory retention for the familiar object.

Seizure Susceptibility

This trait was evaluated in PND21 mice after acute administration of the compounds or its vehicle, 30 min before starting the procedure. To measure audiogenic seizure sensitivity mice were placed individually into a novel environment, a glass cylinder (40 cm high, 16 cm diameter) and allowed to explore for 1 min. Next, a bell (100 dB) was rung for 30 sec and seizure activity scored according to the following scale: no response, 0; wild running, 1; clonic seizure, 2; tonic seizure, 3; status epilepticus/respiratory arrest/death, 4.

Experimental Protocol

Adult mice (10-15 weeks old) were treated either acutely with one dose of CBDV on PND 21 or were treated once daily with CBDV for 7 consecutive days. Mice were evaluated in the novel object recognition task after the first and sixth day of CBDV administration. Doses of CBDV used were 2, 10, 20, 100 and 200 mg/kg.

Results

FIG. 3A shows the acute treatment had no effect on the discrimination index for knockout Fmr1 mice at any of the doses administered. At the lowest dose of 2 mg/kg CBDV there was an increase of the discrimination index in the knockout mice over that of the vehicle treated mice however this was not significant, nor did it reach the values considered to reflect memory retention.

FIG. 3B demonstrates that after chronic treatment (once daily for 7 days) with CBDV at doses of 20 and 100 mg/kg there was a statistically significant increase in the discrimination index in the knockout mice over the vehicle treated knockout mice.

The discrimination index level are both over 0.3 and as such are considered to represent that the mice treated with these doses of CBDV were able to retain memory for familiar objects.

On postnatal day 21 (PND21) WT and Fmr1 KO mice were injected with CBDV (2, 10, 20 or 100 mg/kg) or vehicle, 30 min before exposure to a bell ring (100 dB). Mice exposed to this noise for 30 sec ceased from their normal exploratory behaviour and reacted with gradually to wild-running, clonic seizure, tonic seizure or death. The maximum response was annotated for each mouse as detailed in Table 2 below. A score was calculated according to the severity of the symptoms as explained in the Methods section.

As can be seen the FXS mice provided with the highest dose of 100 mg/kg CBDV remained seizure free whereas those on the lower doses experienced seizures of varying severity.

TABLE 2

Susceptibility to audiogenic seizures in Fmr1 KO and WT mice (PND21) after acute (30 min) administration of CBDV or vehicle

| WT | Vehicle n = 6 | CBDV (2 mg/kg) n = 6 | CBDV (10 mg/kg) n = 5 | CBDV (20 mg/kg) n = 6 | CBDV (100 mg/kg) n = 6 |
|---|---|---|---|---|---|
| No response | 6 | 6 | 5 | 5 | 6 |
| Wild running | 0 | 0 | 0 | 1 | 0 |
| Clonic seizure | 0 | 0 | 0 | 0 | 0 |
| Tonic seizure | 0 | 0 | 0 | 0 | 0 |
| Death | 0 | 0 | 0 | 0 | 0 |

| FXS | Vehicle n = 7 | CBDV (2 mg/kg) n = 5 | CBDV (10 mg/kg) n = 5 | CBDV (20 mg/kg) n = 5 | CBDV (100 mg/kg) n = 5 |
|---|---|---|---|---|---|
| No response | 2 | 2 | 0 | 2 | 5 |
| Wild running | 3 | 1 | 3 | 1 | 0 |
| Clonic seizure | 0 | 0 | 0 | 0 | 0 |
| Tonic seizure | 2 | 2 | 2 | 2 | 0 |
| Death | 0 | 0 | 0 | 0 | 0 |

Conclusions

These data demonstrate that the treatment of 20 and 100 mg/kg CBDV once daily for 7 days to mice which were deficient in the Fmr1 gene and subsequently suffered similar cognitive deficits to individuals with FXS, were able to reverse these cognitive deficits.

Furthermore at the higher dose of CBDV (100 mg/kg) the compound was able to completely eliminate the seizures that occur in the FXS type mice.

As such CBDV is considered to be a viable treatment option for FXS.

Example 3: Use of Cannabidivarin (Cbdv) in A Mouse Model of Rett Syndrome

The phytocannabinoid cannabidivarin (CBDV) was evaluated in a mouse model of Rett syndrome (RS). Such model evaluates the treatment on motor alterations and cognitive deficits present in MeCP2 KO mice.

CBDV was administered daily at the dose of 2, 20 and 200 mg/kg i.p. starting from PND 28 and the following signs were scored every other day: hindlimb clasping (indication of motor imbalance), tremor, gait (measure of coordination), breathing, mobility and general condition.

Furthermore, the efficacy of CBDV in reverting/attenuating the short- and long-term memory deficits present in these mice was evaluated. The Novel Object Recognition (NOR) test was performed before the starting of the treatment Post Natal Day 28 (PND 28), at PND 41 when the first motor symptoms appear and at PND 56 and 66 when the disease is fully manifested.

Materials and Methods

The CBDV was dissolved in ethanol, cremophor and saline (1:1:18).

Starting from PND 28, mice received a daily intraperitoneal injection of CBDV (or vehicle) at the dose of 2, 20 and 200 mg/kg. Animals were then scored every other day to evaluate the effect of CBDV treatment on motor symptoms (hindlimb clasping, gait, mobility) as well as neurological signs and general conditions (breathing abnormalities, tremors and general condition) present in MeCP2 knockout (KO) mice.

Symptom Scoring

Each of the six symptoms was scored from 0 to 2 (0 corresponds to the symptom being absent or the same as in the wild type (WT) animal; 1 when the symptom was present; 2 when the symptom was severe).

Mobility: the mouse is observed when placed on bench, then when handled gently. 0=as WT. 1=reduced movement when compared with WT: extended freezing period when first placed on bench and longer periods spent immobile. 2=no spontaneous movement when placed on the bench; mouse can move in response to a gentle prod or a food pellet placed nearby.

Gait: 0=as WT. 1=hind legs are spread wider than WT when walking or running with reduced pelvic elevation, resulting in a 'waddling' gait. 2=more severe abnormalities: tremor when feet are lifted, walks backward or 'bunny hops' by lifting both rear feet at once.

Hindlimb clasping: mouse observed when suspend by holding base of the tail. 0=legs splayed outward. 1=hindlimbs are drawn toward each other (without touching) or one leg is drawn into the body. 2=both legs are pulled in tightly, either touching each other or touching the body.

Tremor: mouse observed while standing on the flat palm of the hand. 0=no tremor. 1=intermittent mild tremor. 2=continuous tremor or intermittent violent tremor.

Breathing: movement of flanks observed while animal is standing still. 0=normal breathing. 1=periods of regular breathing interspersed with short periods of more rapid breathing or with pauses in breathing. 2=very irregular breathing-gasping or panting.

General condition: mouse observed for indicators of general well-being such as coat condition, eyes and body stance. 0=clean shiny coat, clear eyes, and normal stance. 1=eyes dull, coat dull/un-groomed, and somewhat hunched stance. 2=eyes crusted or narrowed, piloerection, and hunched posture.

At PND 28, 41, 56 and 66 the effect of CBDV on short- and long-term memory deficits was investigated through the Novel Object Recognition (NOR) test.

Novel Object Recognition (NOR) Test

The experiment was performed as previously described (Zamberletti E. et al. 2014 and Kruk-Slomka M. et al. 2014).

The experimental apparatus used for the Novel Object Recognition test was an open-field box (43×43×32 cm) made of Plexiglas, placed in a dimly illuminated room. Animals performed each test individually.

Briefly, each animal was placed in the arena and allowed to explore two identical previously unseen objects for 10 minutes (familiarization phase). After an inter-trial interval of 30 minutes and 24 hours one of the two familiar objects was replaced by a novel, previously unseen object and mice were returned to the arena for the 10-minute test phase.

During the test phase the time spent exploring the familiar object (Ef) and the new object (En) was recorded separately by two observers blind to the groups and the discrimination index was calculated as follows: $[(En-Ef)/(En+Ef)] \times 100$.

Results

Figure 4A:
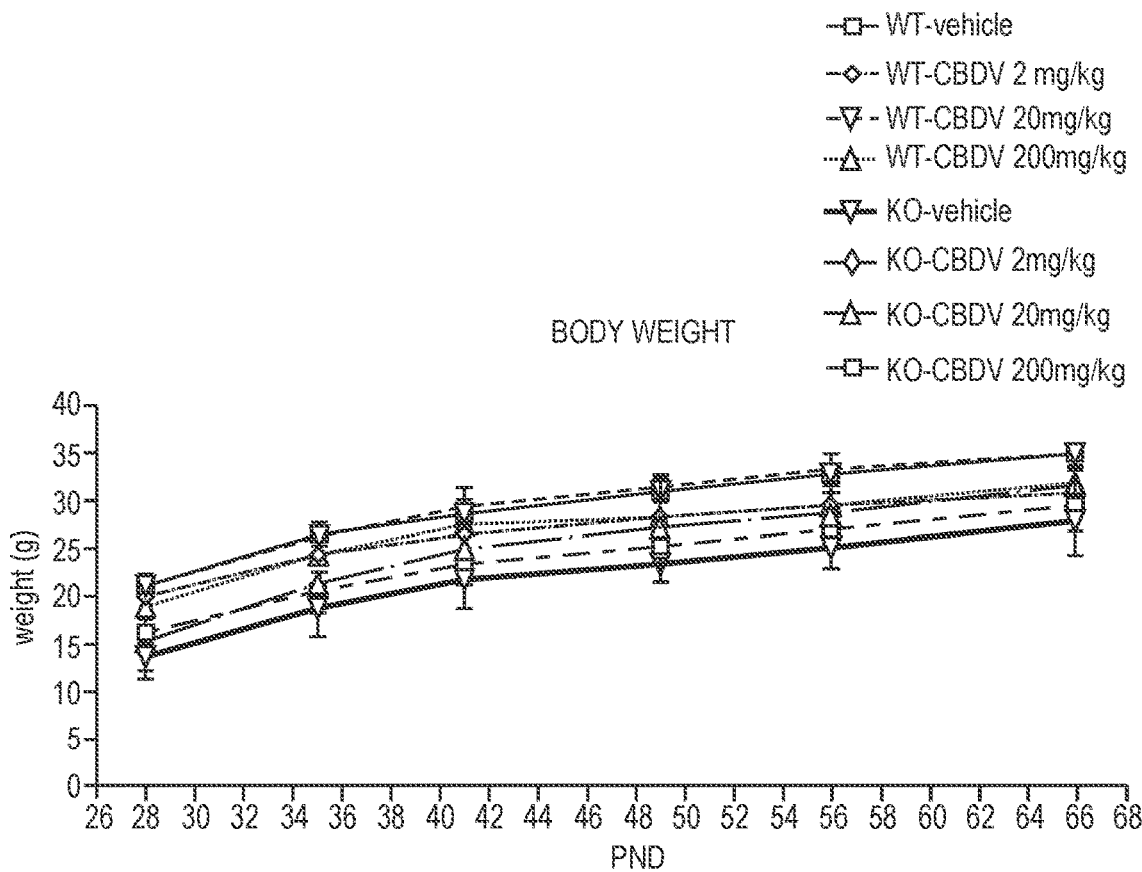
FIG. 4 A-B shows the effect of CBDV on bodyweight in a mouse model of Rett syndrome.

FIG. 4A shows the effect of CBDV (2, 20 and 200 mg/kg) on body weight gain in KO and wild type animals. Analysis of body weight gain as measured during the entire treatment period (PND 28-66) revealed that KO mice treated with vehicle were leaner than controls.

Treatment with CBDV 2, 20 and 200 mg/kg was able to partially prevent the reduction in body weight present in MeCP2 KO mice.

Figure 4B:
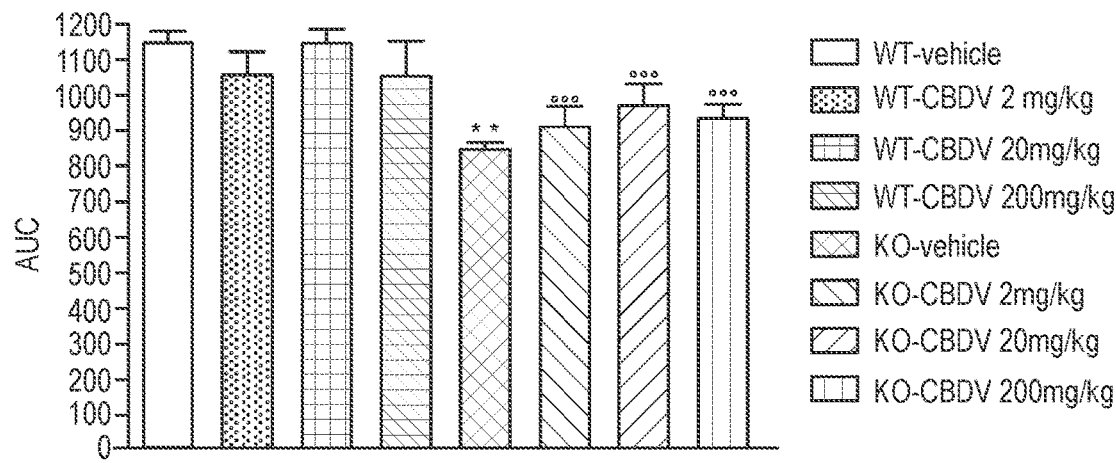

This was evident when the area under the curve (AUC) was calculated (FIG. 4B), clearly showing that body weight of KO mice treated with vehicle was significantly lower than WT mice and treatment with CBDV significantly rescued body weight in KO mice without affecting body weight in WT controls.

Figure 5:
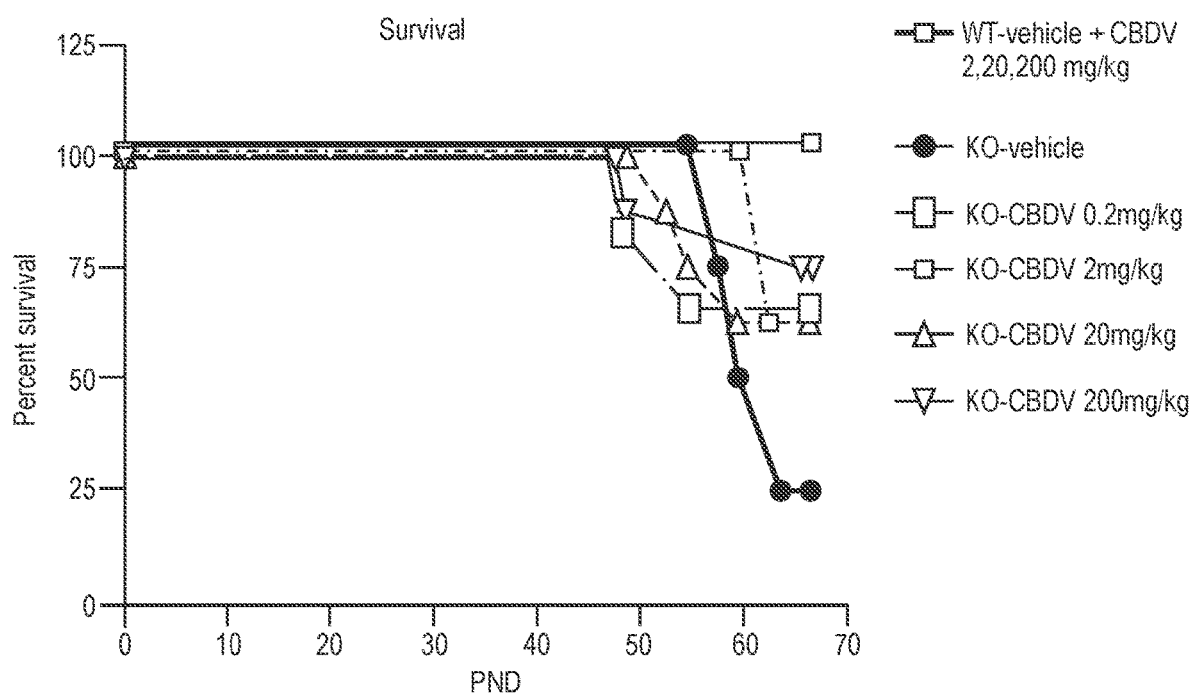
FIG. 5 shows the effect of CBDV on survival in a mouse model of Rett syndrome.
Figure 6A:
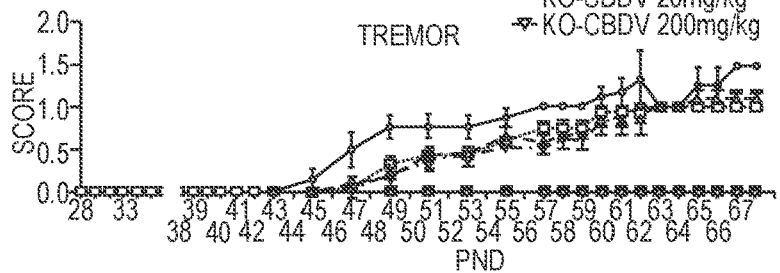
FIG. 6 A-D shows the effect of CBDV on symptoms in a mouse model of Rett syndrome.
Figure 6B:
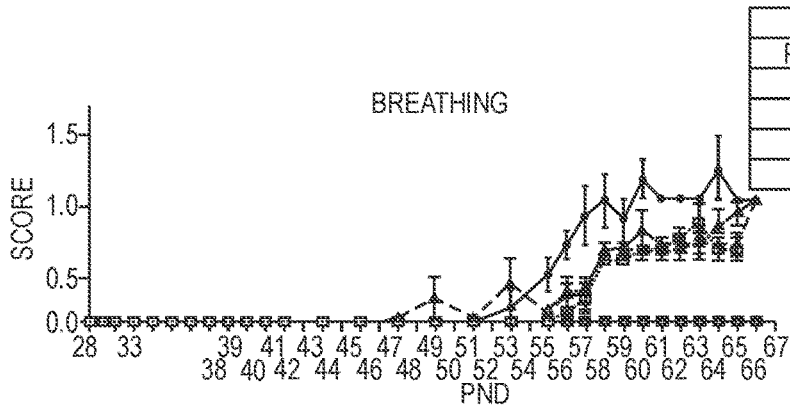
Figure 6C:
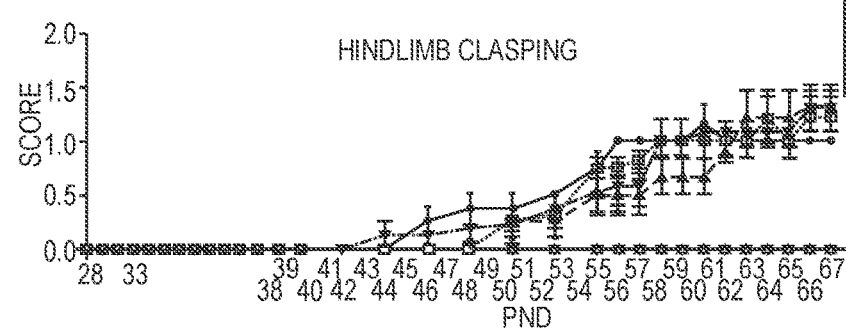
Figure 6D:
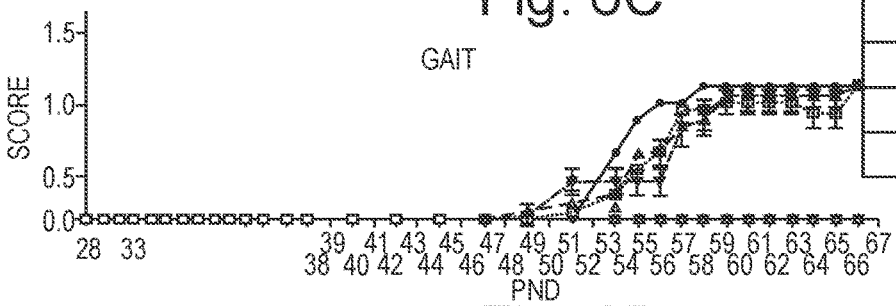

FIG. 5 shows the percentage of survival of MeCP2 KO and WT mice treated with three different doses of CBDV (2, 20 and 200 mg/kg). The results are displayed as percent survival with respect to the time (PND).

No lethality was observed for WT mice treated with vehicle or CBDV. In contrast, analysis of survival measured at PND 67 revealed that CBDV at all three doses tested was able to increase survival in KO mice.

In particular, survival rates were 62.5% in KO mice treated with CBDV 2 and 20 mg/kg and 75% in those treated with 200 mg/kg, compared with 25% of KO mice treated with vehicle.

Figure 7A:
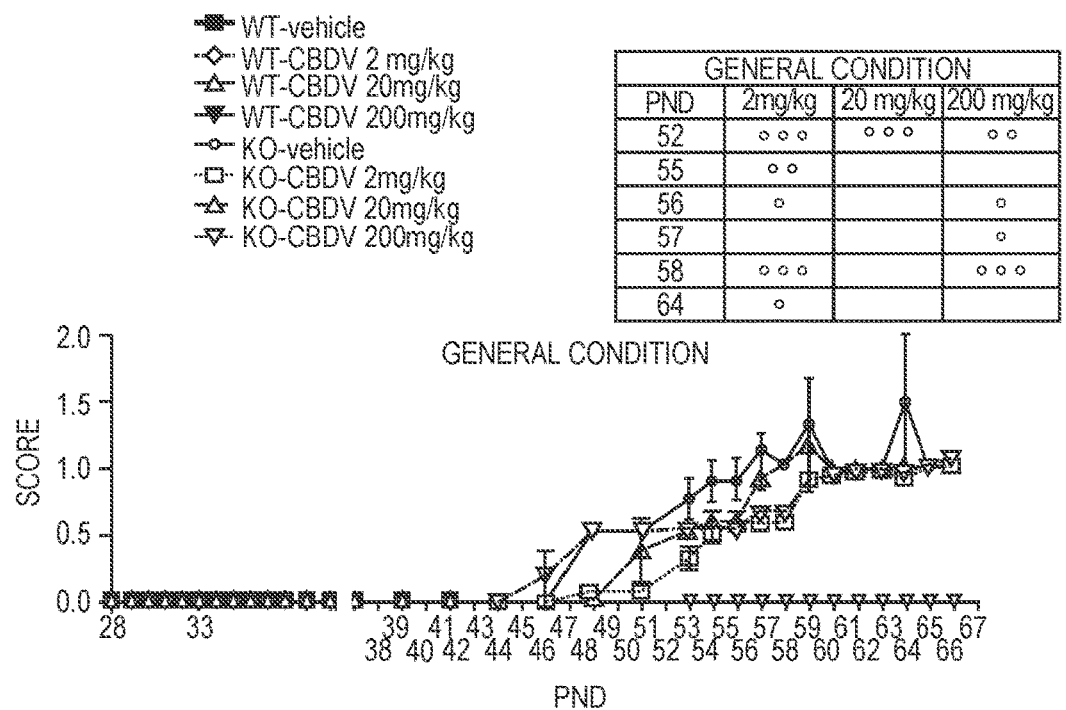
FIG. 7 A-B shows the effect of CBDV on symptoms in a mouse model of Rett syndrome.
Figure 7B:
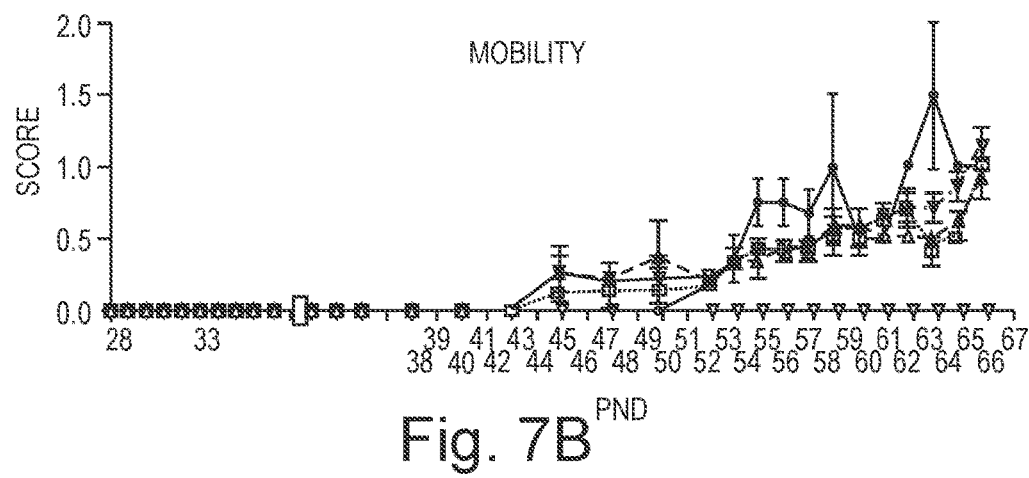

FIGS. 6 and 7 describes the effect of chronic CBDV (2, 20 and 200 mg/kg) on six different signs of the phenotype (FIG. 6A tremor; 6B breathing; 6C hindlimb clasping; 6D gait, FIG. 7A general condition and 7B mobility) in KO mice at different stages of the disease.

All three doses of CBDV were effective in significantly delaying and reducing tremors in KO mice in the first stages of the disease (PND 45-49), whereas only 200 mg/kg dose was still able to reduce tremors at later stages of the disease (PND 55 and 63). The lower dose, 2 mg/kg, was still protective at the later time point (PND 63).

Similarly, CBDV administration was able to improve breathing in KO mice. This improvement was more pronounced in KO mice treated with CBDV 2 mg/kg. CBDV 2 mg/kg significantly improve breathing from PND 56 to 60, whereas CBDV 20 mg/kg showed a significant effect at PND 57 and CBDV 200 mg/kg was effective at PND 57 and 60.

The lower doses of CBDV were also able to significantly attenuate hindlimb clasping at PND 47 and 49, whereas CBDV 200 mg/kg did not significantly affect this parameter. Conversely, CBDV 200 mg/kg significantly improved gait from PND 53 to 57.

General conditions of KO mice (coat and eyes conditions) were significantly improved after treatment with CBDV 2 and 200 mg/kg (PND 52-64); whereas the dose of 20 mg/kg was significantly effective only at the earlier time point (PND 52). CBDV effect on mobility was less intense, as it reached statistical significance only at PND 64.

Figure 8:
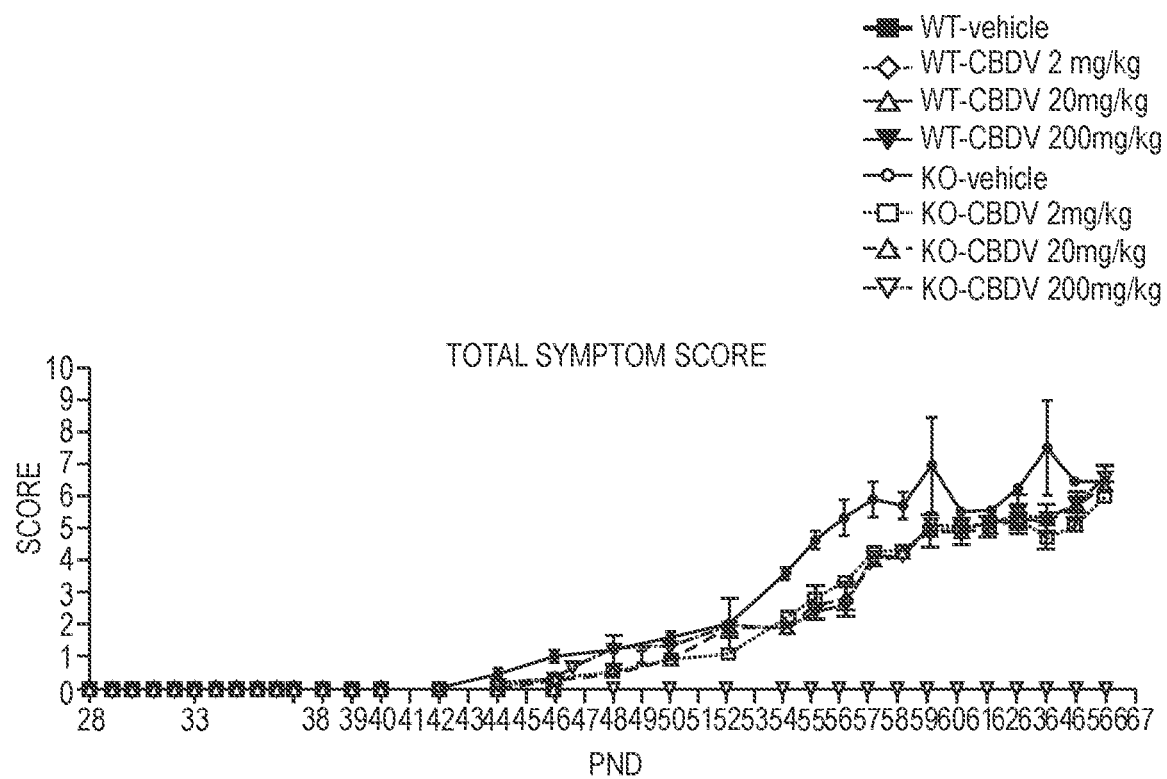
FIG. 8 shows the effect of CBDV on total symptom score in in a mouse model of Rett syndrome.

To better analyse the effect of chronic CBDV (2, 20 and 200 mg/kg) on progression of the signs in KO animals the single scores were grouped in a total symptom score that is represented in FIG. 8.

The total symptom score confirms the observation that CBDV treatment at all three doses tested is able to delay and attenuate the appearance of the phenotype in KO mice as compared with KO-vehicle animals.

The dose of 2 mg/kg significantly improved total symptom score at every time point (PND 45, 47, 49, 55, 56, 57, 58, 60 and 64). The 20 mg/kg dose had a similar effect, but was less effective at the later time point (PND 64). The 200 mg/kg dose exerted beneficial effect at a later time point (PND 47) and its protective effect was evident until PND 58.

Figure 9:
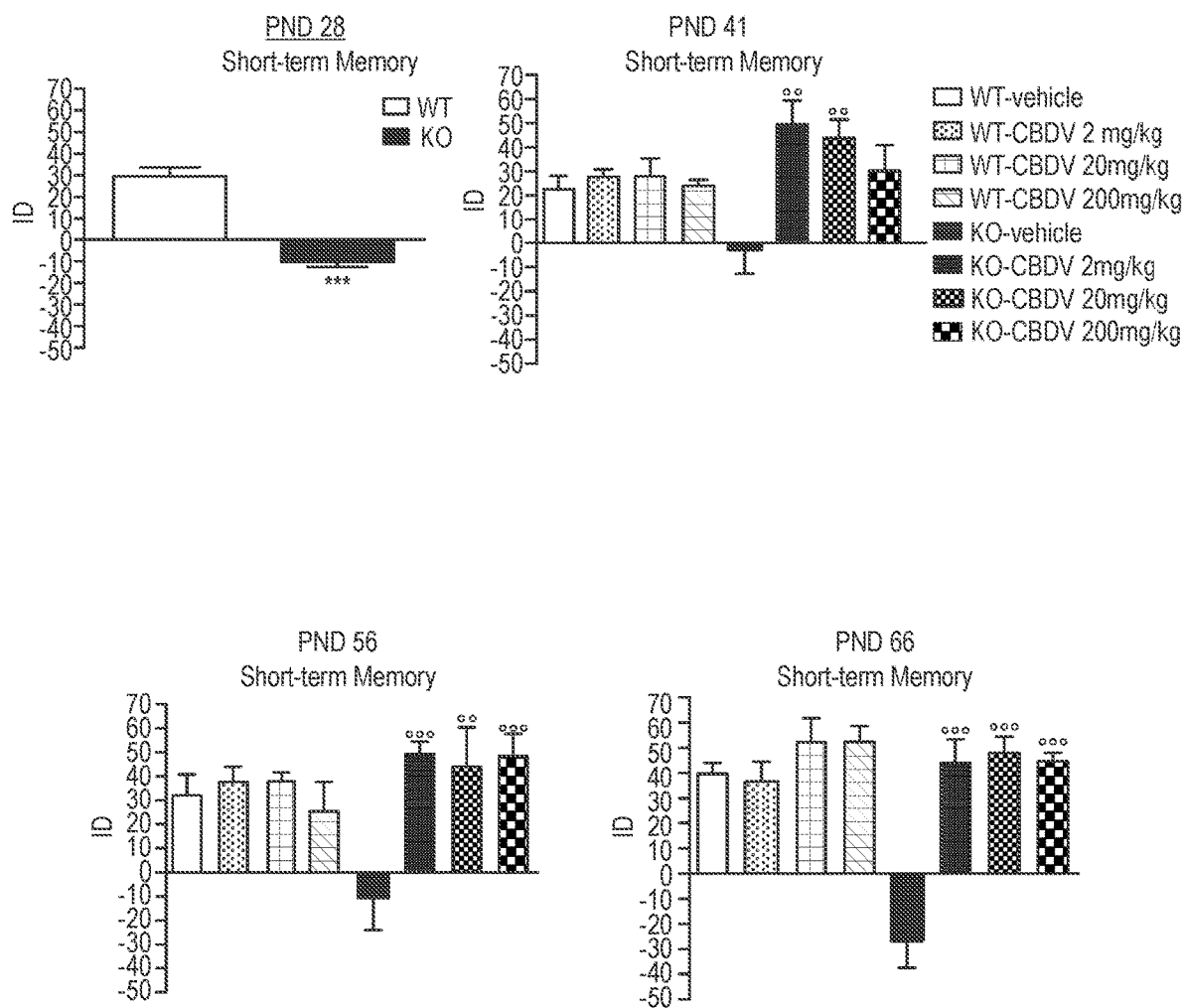
FIG. 9 shows the effect of CBDV on short-term memory in a mouse model of Rett syndrome.

FIG. 9 shows the effect of CBDV (2, 20 and 200 mg/kg) on short-term memory in the NOR test at different ages.

In KO animals, a significant cognitive impairment in short-term memory was found at PND 28, a time point when the motor symptoms are not present. This impairment was still present and significant at PND 41, 56 and 66, when the disease is fully manifested.

At each considered time point, administration of the three different doses of CBDV significantly reverted the cognitive impairment in short-term memory present in KO mice without affecting recognition memory when administered to WT littermates.

Figure 10:
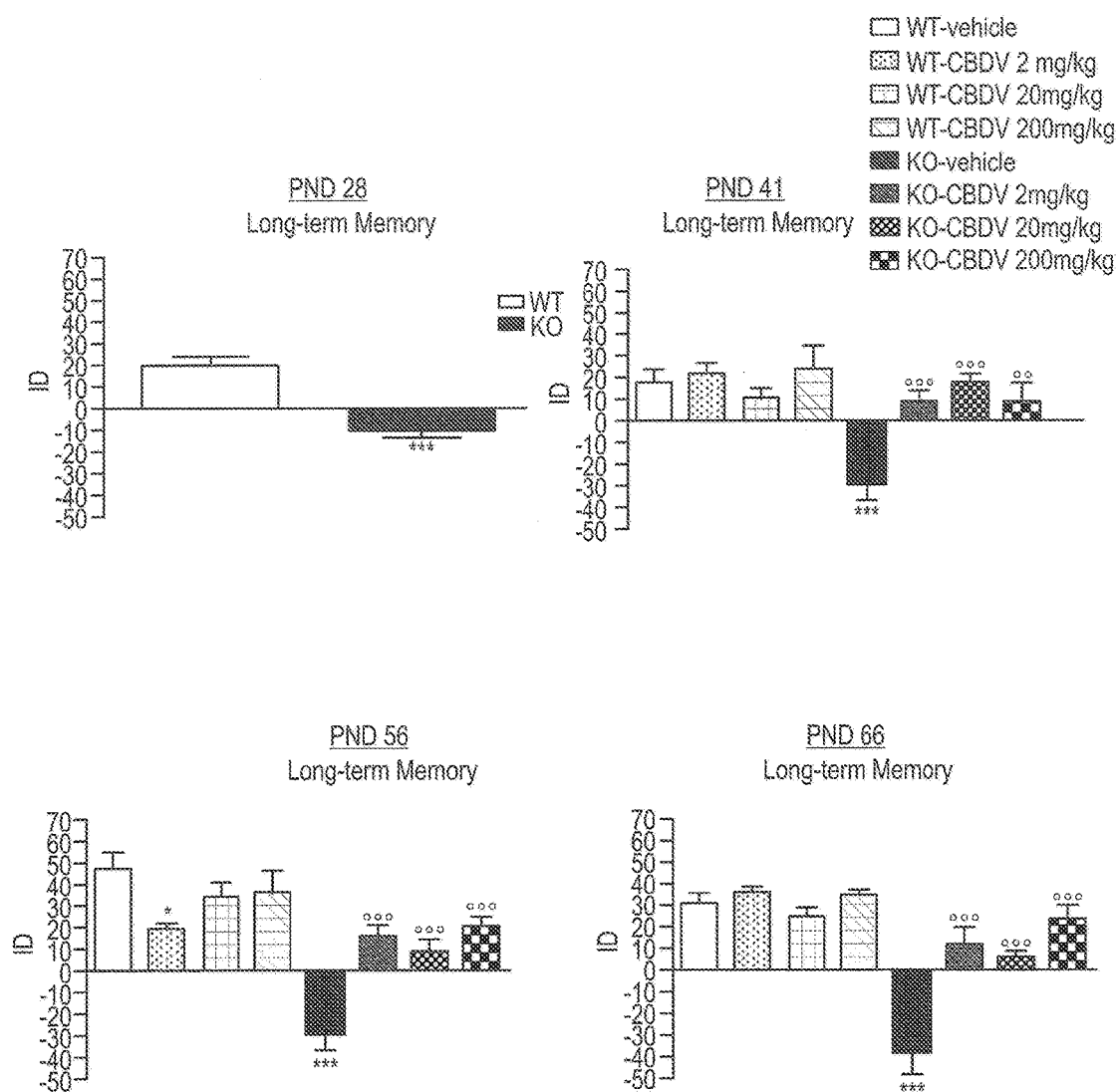
FIG. 10 shows the effect of CBDV on long-term memory in a mouse model of Rett syndrome.

FIG. 10 shows the effect of CBDV (2, 20 and 200 mg/kg) on long-term memory in the NOR test at different ages.

Similar to what has been observed for short-term memory; all three doses of CBDV administered were also able to significantly counteract the cognitive impairment in long-term memory present in KO mice without affecting recognition memory when administered to WT littermates.

Conclusions

These data demonstrate that CBDV treatment was effective in delaying and attenuating the phenotype of MeCP2 KO mice. The CBDV treatment was able to significantly recover the deficits in short- and long-term memory present in those animals.

Moreover all doses tested had similar beneficial effects in attenuating the phenotype and reversing the cognitive deficits.

Besides the beneficial effect in terms of total symptoms appearance, it must be underlined the striking recovery of the cognitive deficits induced by CBDV in MeCP2 KO mice, that is still present and significant also at very late stages of the disease (PND 66).

Importantly the survival rates in KO mice treated with CBDV is in a range between 62.5 and 75% with respect to the value of 25% in KO mice treated with vehicle.

These data indicate that CBDV offers a significant treatment option in the treatment of RS.

Example 4: Use of Cannabidivarin (Cbdv) in A Mouse Model of Angelman Syndrome The effect of CBDV was tested in the treatment of neurological, behavioural and motor disorders and seizures in a transgenic mouse model of Angelman Syndrome.

Materials and Methods

Animals

Heterozygous mice with maternal deficiency of Ube3A (Ube3am−/p+) and wild type (Ube3am+/p+) were purchased from The Jackson Laboratory (Jackson code: B6.129S7-Ube3a tm1Alb/J) and maintained in a C57BL/6 background.

Animals were housed under controlled illumination (12:12-hour light/dark cycle; light on 6 hours) and environmental conditions (room temperature: 20° C.–22° C., humidity: 55%-60%) with food and tap water were available ad libitum.

Drugs and Treatment

Drugs were dissolved in 1:1:18 ethanol:cremophor:0.9% saline, for intraperitoneal (i.p.) administration. Drug treatment was performed daily for 35 days. CBDV was administered at 20 mg/kg.

For the audiogenic seizure tests CBDV was administered at 20, 200 and 400 mg/kg.

Behavioural Tests

Rotarod: The rotarod test assesses balance and motor coordination of mice. Mice have been measured for the time (in seconds) of equilibrium before falling on a rotary cylinder by a magnet that, activated from the fall of the mouse on the plate, allows to record the time of permanence on the cylinder. After a period of adaptation of 30 s, the spin speed gradually increased from 3 to 30 rpm for a maximum time of 5 min. The animals were analysed by 2 separate tests at 1-h interval in the same day.

Clasping: The clasping test assesses ataxia in mice. Mice were suspended by the base of the tail and their behaviours were recorded for 30 seconds. The time for which the mice clasped their hind limbs was recorded. The time was then scored as follows: 4, 15-30 s, 3, 10-15 s, 2, 5-10 s, 1, 0-5 s and 0,0 s Tail suspension: The tail suspension test assesses depressive-like behaviour in mice. Mice were individually suspended by the tail on a horizontal bar (50 cm from floor) using adhesive tape placed approximately 4 cm from the tip of the tail. The duration of immobility was recorded in seconds over a period of 6 minutes by a time recorder. Immobility time was defined as the absence of escape-oriented behaviour.

Novel Object Recognition: The novel object recognition assesses recognition memory in mice. The experiment started with the habituation period, during which mice were allowed to freely explore for 1 hour the apparatus which consists of a rectangular open box (40×30×30 cm width×length×height) made of grey polyvinyl chloride (PVC) illuminated by a dim light. The day after each mouse was allowed to explore two identical objects positioned in the back left and right corners for 5 min (acquisition). A video camera recorded the time spent on exploration of each object. In the test trial, which was carried out for 2 hrs after the acquisition, one of the two objects was replaced with a new different object. The time spent exploring the object was the time that the mouse spent with its nose directed and within 1 cm from the object. The behaviour of mice was analyzed by an observer blind to the treatment. Data are expressed as percentage of recognition index (RI %), which was calculated as the percentage of the time spent exploring the novel object/time spent exploring the novel object+time spent exploring the familiar object×100.

Seizure susceptibility: Audiogenic seizures were induced by vigorously scraping scissors across the metal grating of the cage lid which produces a 100 DB high frequency loud noise. This was done for 20 seconds. This test consists of 3 phases. In phase 1 all mice were tested for epilepsy. In phase 2 all mice were injected daily with either vehicle or a drug for 7 or 10 days. In phase 3 mice were tested for epilepsy (one hour after last injection).

Statistical Analysis: Behavioural data are represented as means±SEM and statistical analysis of these data was performed by two way analysis of variance (ANOVA) for repeated measured followed by the Student Newman-Keuls for multiple comparisons to determine statistical significance between different treated groups of mouse. $p<0.05$ was considered statistically significant.

Results

Figure 11:
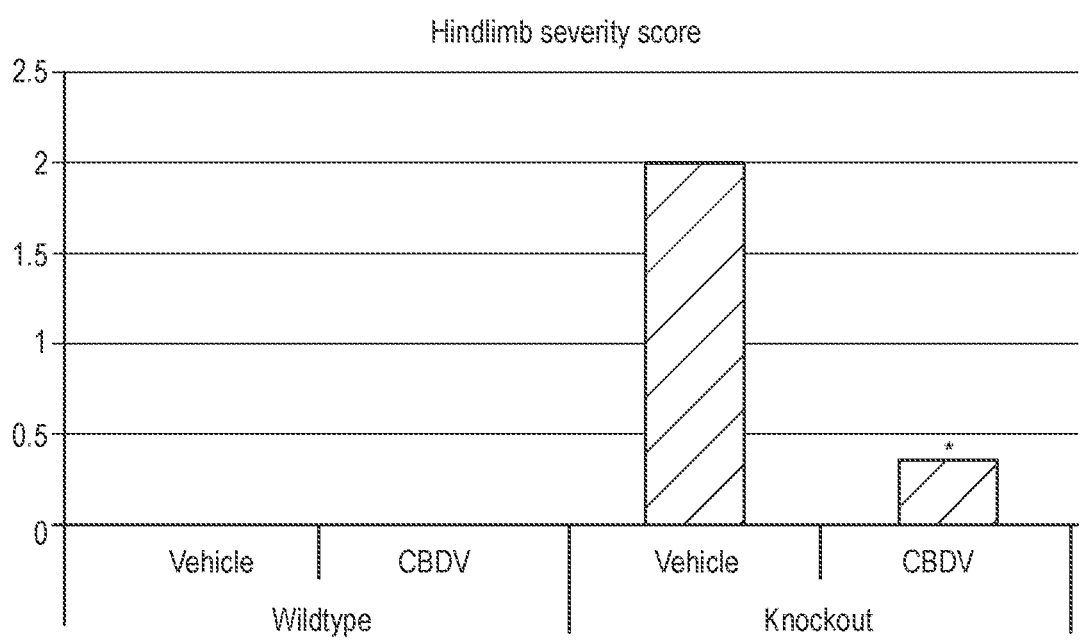
FIG. 11 shows the effect of CBDV on clasping duration in a mouse model of Angelman syndrome.

FIG. 11 shows that AS mice treated with vehicle showed significantly longer clasping duration at 10 weeks of age compared to WT mice treated with vehicle. In AS mice chronic treatment (30 days) with CBDV significantly reduced clasping duration at 10 weeks of age compared to AS mice treated with vehicle.

Figure 12:
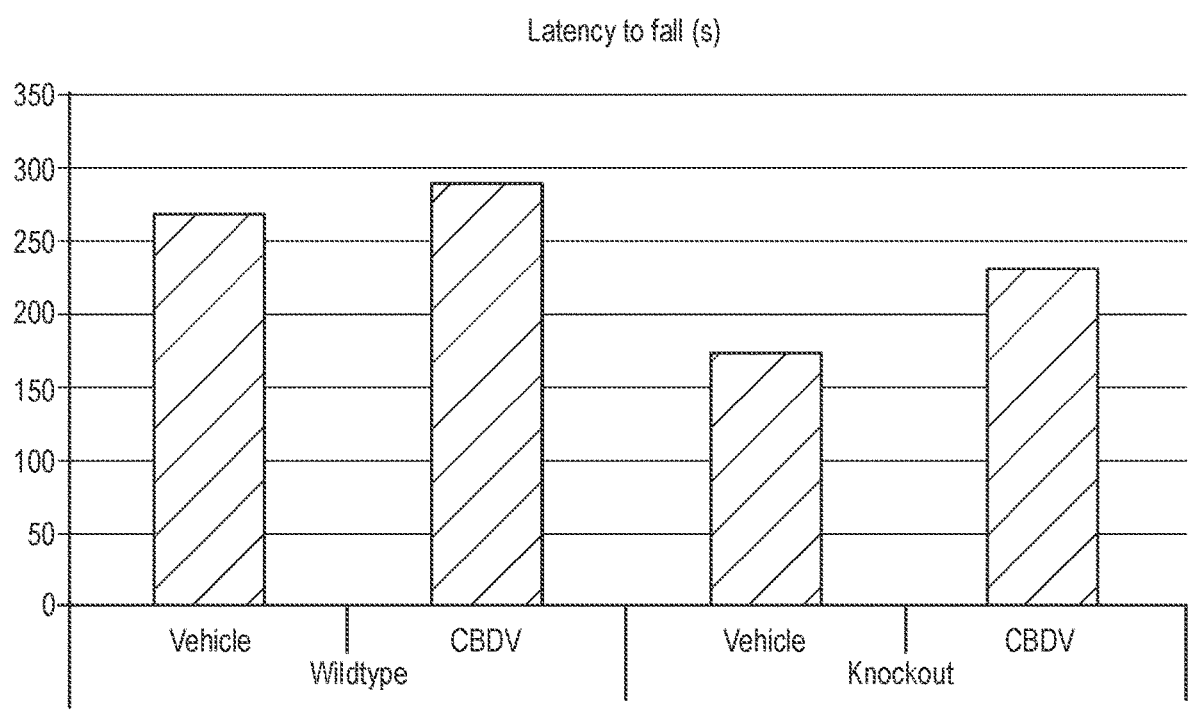
FIG. 12 shows the effect of CBDV in the rotarod test in a mouse model of Angelman syndrome.

FIG. 12 demonstrates that AS mice treated with vehicle showed a significant motor impairment at 10 weeks of compared to WT mice treated with vehicle. In AS mice, chronic treatment (30 days) with CBDV reduced latency to fall compared to AS mice treated with vehicle.

Figure 13:
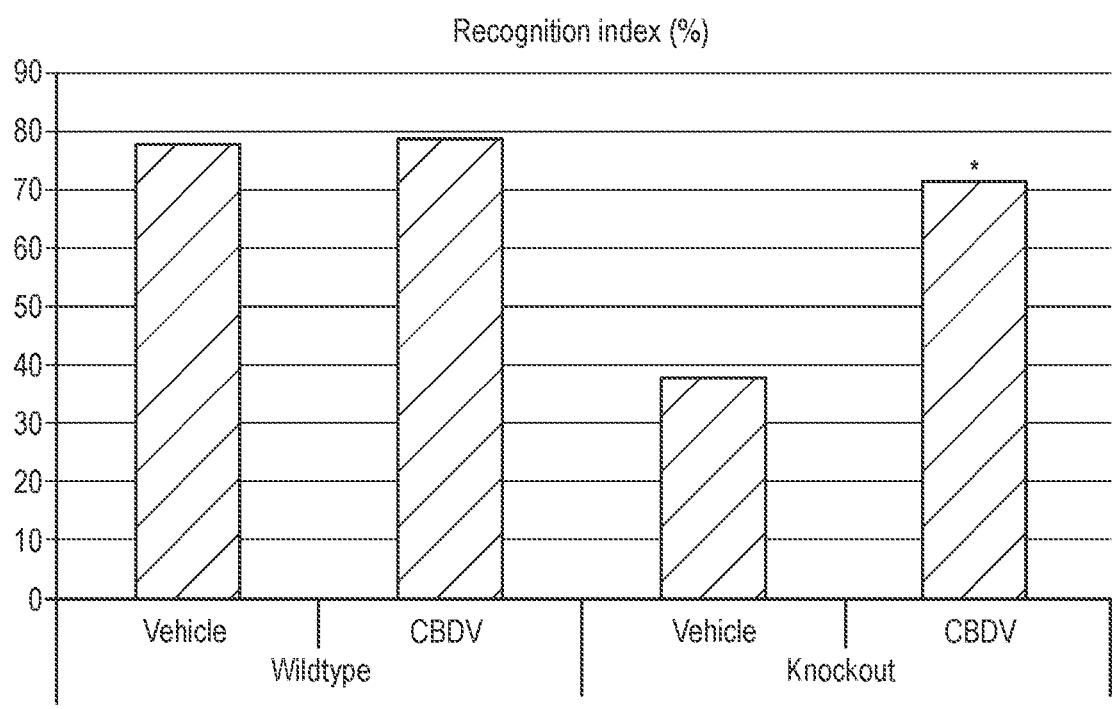
FIG. 13 shows the effect of CBDV in the novel object recognition test in a mouse model of Angelman syndrome.

Mice were assessed at the age of 7-8 weeks in the novel object recognition test. AS mice treated with vehicle showed a significant decrease in the discrimination index compared with WT mice that received the same treatment. FIG. 13 shows that AS mice treated with CBDV significantly increased the discrimination index compared to AS mice treated with vehicle.

Figure 14:
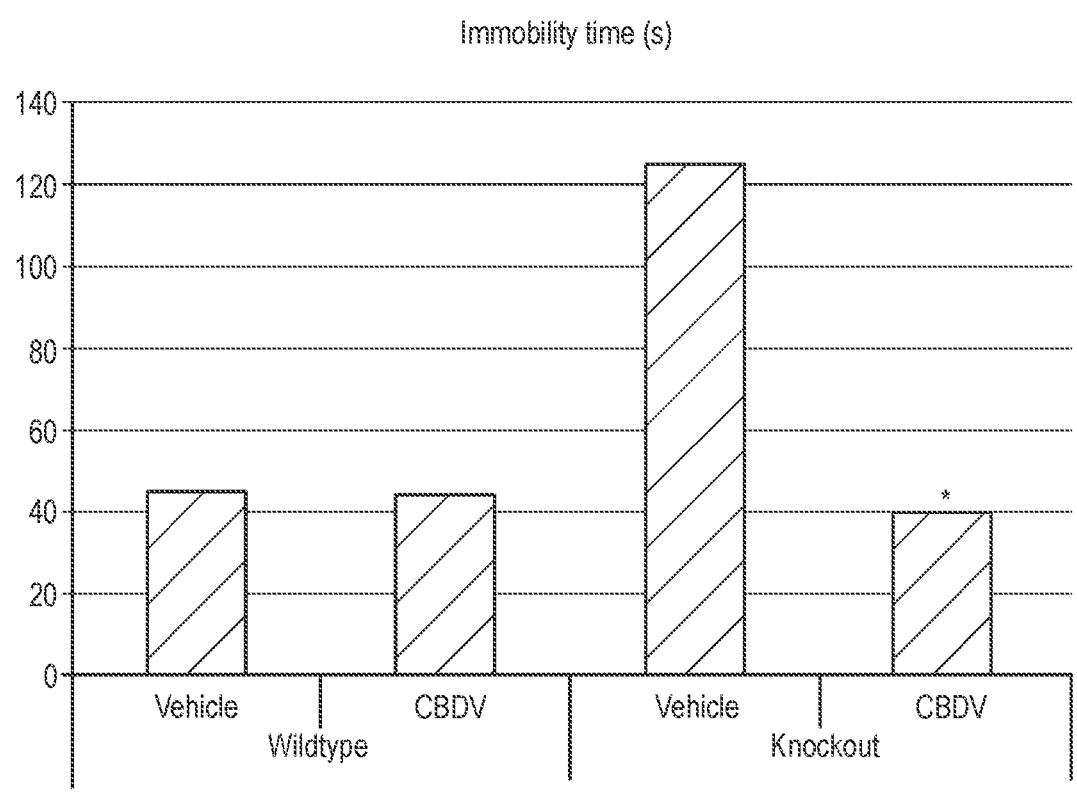
FIG. 14 shows the effect of CBDV in the tail suspension test in a mouse model of Angelman syndrome.

FIG. 14 shows that in the tail suspension test the time of immobility were significantly higher in AS mice that received vehicle compared to WT mice that received the same treatment. In AS mice treatment with CBDV significantly reduced the duration of immobility time compared to AS mice treated with vehicle.

Figure 15:
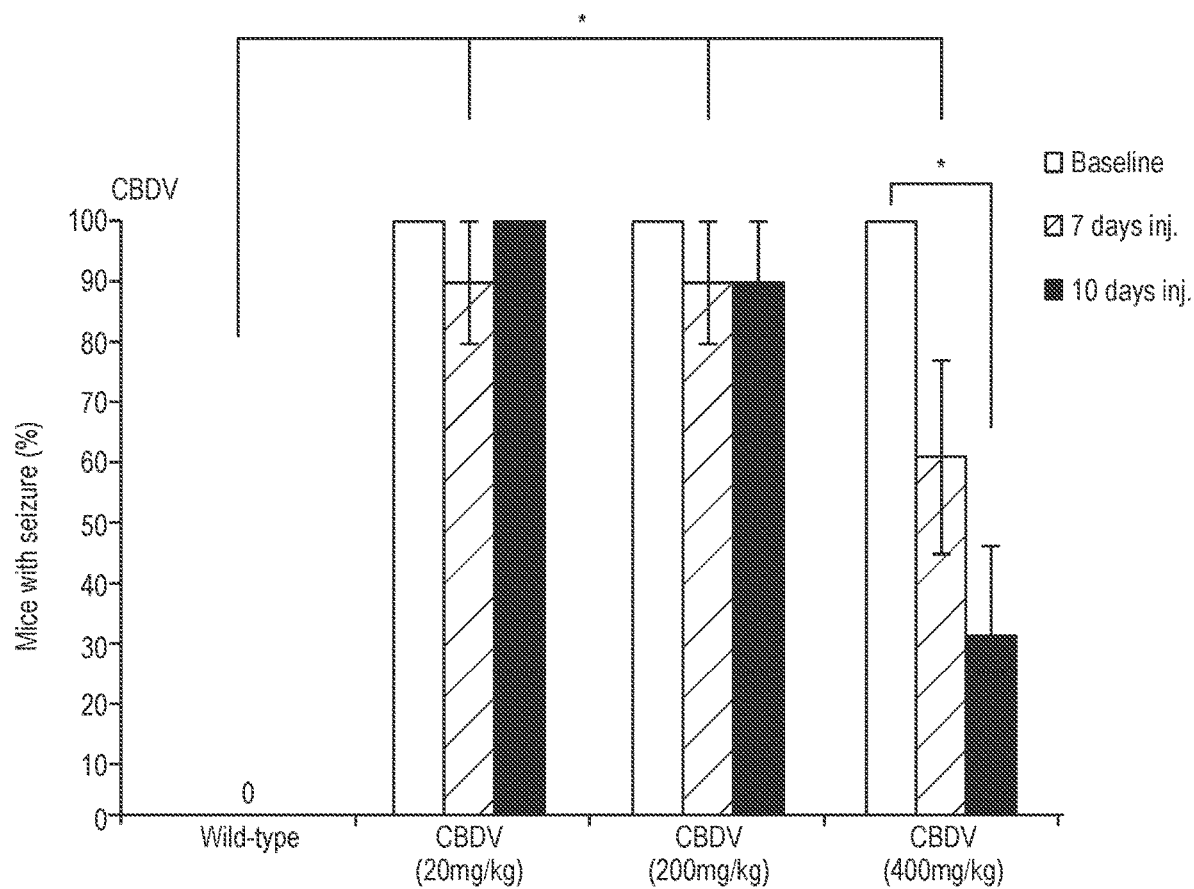
FIG. 15 shows the effect of CBDV on audiogenic seizures in a mouse model of Angelman syndrome.

FIG. 15 demonstrates that the wildtype mice were not susceptible to audiogenic seizures. CBDV administered at 20 mg/kg or 200 mg/kg had no effect on the seizure susceptibility as there was very little change in the number of mice with seizures compared to baseline after either 7 or 10 days treatment. However in the mice treated with 400 mg/kg CBDV there was a statistically significant decrease in the number of mice with seizures, whereby after 7 days treatment the number of mice experiencing seizures dropped from 100% down to 60% and after 10 days treatment this number had decreased further to 30%.

Conclusion

These data demonstrate that the treatment of 20 mg/kg CBDV to mice which were deficient in the Ube3A gene and subsequently suffered similar cognitive deficits to individuals with AS, were able to reverse these cognitive deficits.

Furthermore at a higher dose of 400 mg/kg CBDV was able to reduce the seizure susceptibility of Angelman mice by 70% after 10 days treatment.

As such CBDV is considered to be a viable treatment option for AS.

Example 5: Use of Cannabidivarin (Cbdv) in A Rat Model of Schizophrenia

The phytocannabinoid cannabidivarin (CBDV) was evaluated in a rat model of schizophrenia.

These data demonstrate the ability of CBDV (2, 10 and 20 mg/kg), in comparison with the positive control risperidone, to attenuate the disruption of a cognitive task induced by sub-chronic treatment with phencyclidine (PCP) in rats.

The effect of PCP in the novel object recognition (NOR) test is thought to model visual recognition memory deficits similar to those observed in schizophrenia. The atypical antipsychotics, clozapine and risperidone can attenuate the deficit.

A further animal model for assessing the avolition domain of negative symptoms of schizophrenia, lack of social behaviour has also been tested with CBDV using the sub-chronic administration of PCP to rats. PCP induces social behaviour deficit in rats in their interaction with a vehicle treated weight matched control rat.

Materials and Methods

Animals

Female hooded-Lister rats were used for this experiment. Rats were housed in groups of 5 under standard laboratory conditions under a 12 hr light: dark cycle, lights on at 0700 hr. Testing was carried out in the light phase.

Treatment

Rats were randomly assigned to two treatment groups and treated with vehicle, n=20 (distilled water, i.p.) or Phencyclidine hydrochloride (PCP), n=100 (2 mg/kg, i.p. twice daily for 7-days). PCP was dissolved in distilled water. This was followed by a 7-day wash out period before the rats were tested following acute treatment with CBDV, risperidone or vehicle.

Risperidone (0.1 mg/kg) was dissolved in a minimum volume of acetic acid, made up to volume with distilled water and pH adjusted to 6 with 0.1M NaOH and administered via the i.p. route in a volume of 1 ml/kg, 60 min prior to testing.

CBDV at 2, 10 or 20 mg/kg was dissolved in 2:1:17 (Ethanol:Cremofor:Saline 0.9%) and administered via the i.p. route in a volume of 5 ml/kg, 60 min prior to testing.

Novel Object Recognition Test

Habituation:

Rats were allowed to habituate to the empty test box and the behavioural test room environment for 1h on day 1. Prior to behavioural testing on day 2 rats are given a further 3 min habituation.

Behavioural Testing:

Following the 3 min habituation period, the rats are given two 3 min trials (T1 and T2) which are separated by a 1 min inter-trial interval in the home cage during which the objects are changed. Behaviour in all trials was recorded on video for subsequent blind scoring.

T1=Trial 1, the Acquisition Trial:

In this trial, the animals are allowed to explore two identical objects (A1 and A2) for 3 min.

T2=Trial 2, the Retention Trial:

In this trial, the animals explore a familiar object (A) from T1 and a novel object (B) for 3 min. The familiar object presented during T2 is a duplicate of the object presented in T1 in order to avoid any olfactory trails.

Object Exploration:

The object exploration is defined by animals licking, sniffing or touching the object with the forepaws whilst sniffing, but not leaning against, turning around, standing or sitting on the object. The exploration time (s) of each object (A, B, familiar and novel) in each trial are recorded using two stopwatches and the following factors are calculated:

Total exploration time of both objects in the acquisition trial (s).

Total exploration time of both objects in the retention trial (s).

Habituation of exploratory activity includes the exploration time, as measured by the number of lines crossed, for both the trials.

Discrimination index (DI), which is calculated as shown below:

$$\frac{(\text{Time spent exploring novel object} - \text{time spent exploring familiar object})}{\text{Total time spent in exploring the objects}}$$

Social Interaction Test

The social interaction test is performed in an open-field comprising a square box made of Plexiglas (52×52×31 cm) placed 27 cm above the floor on a moveable trolley. The floor of the box is white with black gridlines forming 9 identical squares on it. All other walls are black. A video camera connected to a video recorder and monitor is positioned above the box. The object used for the test consists of a heavy structure made of metal that cannot be displaced by the animals. Care is taken to ensure that these objects do not have natural significance for the rats.

The rats were habituated to the test environment and arena prior to the test day. Habituation consists of placing all rats from one cage together in the empty test arena for one hour for three days including the day before the test day.

Pairs of rats, weight matched (15-20 g) and unfamiliar to each other, receiving either no treatment (n=70 "conspecific" rats) or different treatments (PCP and Vehicle; n=10 "tested" rats or PCP+Drug; n=50 "tested" rats) were placed in the test arena together for 10 min and behaviour assessed as described below.

An inanimate object such as an unopened drinks can is also placed in the centre of the arena to measure any differences in interaction of the test animal with an unfamiliar animal as opposed to an unfamiliar object. After each 10 minute trial, the object and arena are cleaned with 10% alcohol in an attempt to remove traces of any olfactory cues. All testing is carried out under standard room illumination levels (70 cd/m2).

Behaviour in both trials was recorded on video for subsequent blind scoring. A behavioural scoring software program (Hindsight, Scientific programming services) is used to score the following parameters:

Investigative sniffing behaviour: sniffing the conspecific's snout or parts of the body including the anogenital region;

Following: rat moves after the conspecific i.e. a vehicle treated rat of the same species, around the arena;

Avoidances: actively turning away when approached by the conspecific animal;

Investigation of object: exploration of object placed in centre of the arena; and Locomotor activity is recorded by counting the total number of sectors (i.e. lines) crossed by the test rat.

Results

Figure 16:
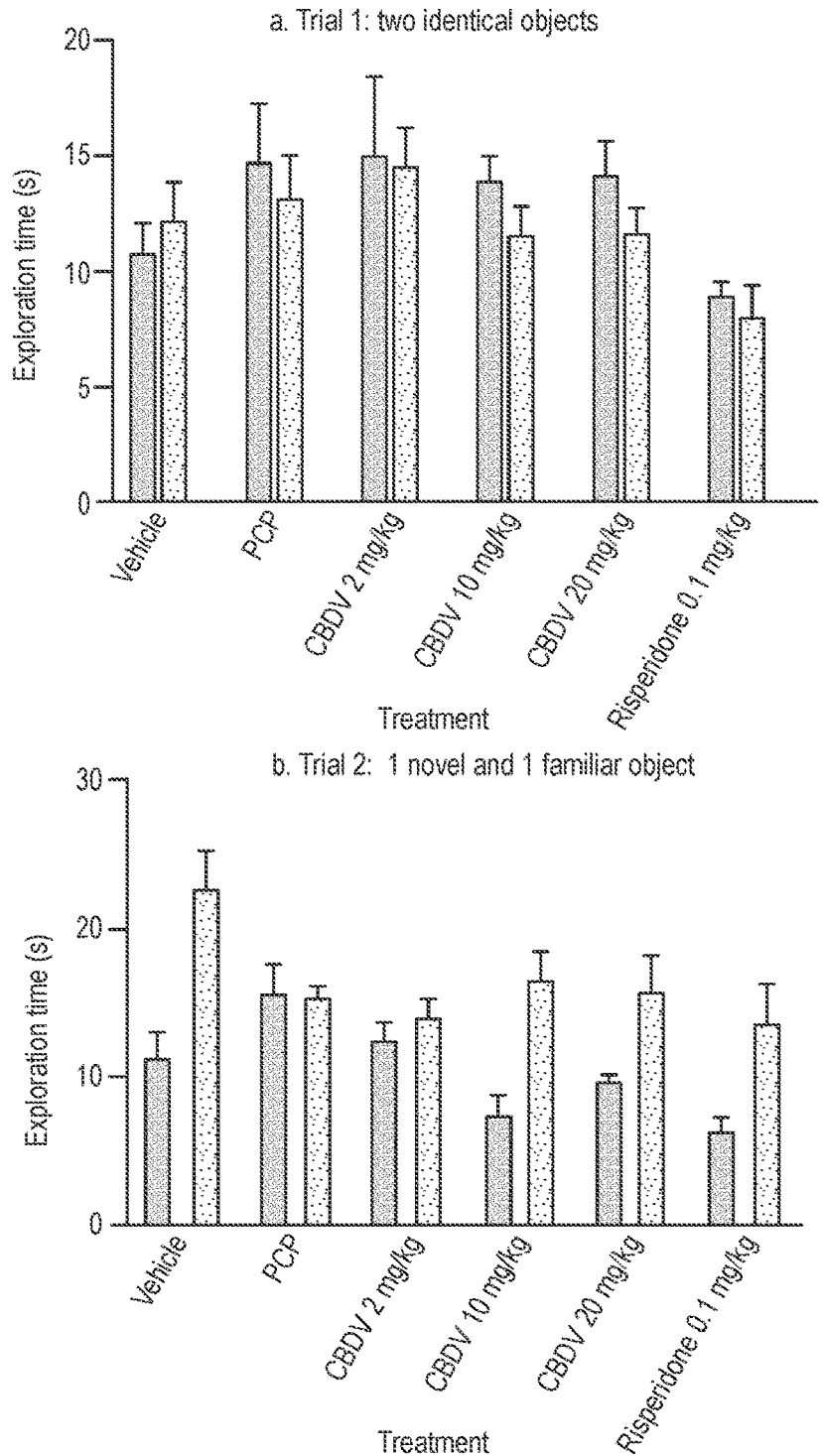
FIG. 16 shows the effect of CBDV in the novel object recognition test in a rat model of schizophrenia.

FIG. 16A shows the time spent investigating two identical objects in Trial 1, as can be seen the rats show no real preference for the two identical objects whether they were treated with CBDV, risperidone or vehicle.

FIG. 16B shows the time spent investigating the two objects when one object is familiar and another is novel. In the PCP treated rats that were not given either CBDV or the positive control risperidone there is no difference between the time spent investigating both objects. In the vehicle treated rats who were not treated with PCP and as such suffered no cognitive dysfunction there was a statistically significant difference between the time spent investigating the objects with a preference for the novel object. This therefore shows that the animals without cognitive dysfunction were able to discriminate between the object that was familiar to them and that which was novel. The PCP treated mice in comparison showed that because of cognitive dysfunction they were unable to remember the object that they had been familiarised with in Trial 1.

FIG. 16B also shows that at a dose of 10 and 20 mg/kg CBDV was able to reverse the cognitive dysfunction brought about in the PCP treated rats such that they were able to discriminate between familiar and novel objects. This effect was also shown in the positive control risperidone.

FIG. 17 shows the discrimination index (DI) for the treatments. In agreement with the data shown in FIG. 15B the rats treated with 10 and 20 mg/kg produced a statistically significant increase in the DI in PCP rats.

FIG. 18 A to C describe the data produced in the social interaction test. As can be seen rats that were treated with PCP showed a decrease in sniffing and following the other rat. In addition treatment with PCP produced an increase in the time spent avoiding the other rat. Taken together these data demonstrate that the PCP treatment produced symptoms of social withdrawal in the rats.

CBDV was able to reverse these effects in a statistically significant manner as was the positive control risperidone. FIG. 18A shows that CBDV at doses of 10 and 20 mg/kg significantly increased the time spent sniffing the other rat. FIG. 18B shows that CBDV at a dose of 20 mg/kg also increased the amount of time spent following the other rat. This effect was not seen to be significant in the positive control risperidone; however the amount of time was increased over that of the PCP alone group.

FIG. 18C demonstrates that CBDV at 20 mg/kg was able to reduce the amount of time the test rat spent avoiding the other rat.

Conclusion

The data described in this example demonstrate that the administration of CBDV to PCP-treated rats was able to treat both the cognitive dysfunction and negative effects which occur in these animals.

Such data demonstrates that CBDV is a suitable treatment option for schizophrenia, in particular symptoms of schizophrenia associated with cognitive dysfunction and negative symptoms such as social withdrawal.

Overall Conclusion

Examples 1 to 5 above describe the use of CBDV in a model of ASD, three models of ASD-associated disorders and a model of schizophrenia. Unexpectedly CBDV has been shown to produce statistically significant reversal of the symptoms associated with these disorders.

In particular CBDV has been shown to produce positive results in the Novel Object Recognition (NOR) test in all models and as such demonstrates unequivocally that this phytocannabinoid could reverse cognitive dysfunction in these disorders.

In addition, other tests in these models provide support that CBDV could be used to treat additional symptoms associated with these disorders. CBDV was able to reduce repetitive behaviours, hyperactivity and sociability in the model of ASD. CBDV was also able to reduce the decrease in bodyweight and survival in a model of Rett syndrome in addition to improvement of overall general condition and symptoms in these animals such as mobility and breathing. Furthermore CBDV was able to reduce ataxia and anxiety symptoms in a model of Angelman syndrome. Lastly CBDV treatment was able to reduce negative symptoms of social withdrawal in a model of schizophrenia.

Taken together CBDV is able to provide an effective treatment option to individuals suffering from ASD, ASD-associated disorders and schizophrenia.

REFERENCES

Hill T et al. (2012) Br J Pharmacol. December; 167(8):1629-42. Cannabidivarin is anticonvulsant in mouse and rat.

Erica Zamberletti, Sarah Beggiato, Luca Steardo Jr., Pamela Prini, Tiziana Antonelli, Luca Ferraro, Tiziana Rubino, Daniela Parolaro. Neurobiology of Disease (2014), Volume 63, Pages 35-47. "Alterations of prefrontal cortex GABAergic transmission in the complex psychotic-like phenotype induced by adolescent delta-9-tetrahydrocannabinol exposure in rats."

Kurz and Blass 2010 Use of dronabinol (delta-9-THC) in autism: A prospective single-case study with an early infantile autistic child. Cannabinoids, 5 (4) 4-6.

Marta Kruk-Słomka, Agnieszka Michalak, Barbara Budzyn'ska, Graz'yna Biała. Pharmacological Reports 66 (2014), 638-646. "A comparison of mecamylamine and bupropion effects on memory-related responses induced by nicotine and scopolamine in the novel object recognition test in mice."

The invention claimed is:

1. A method of treating one or more symptoms or disease characteristics associated with autistic spectrum disorder (ASD) or ASD-associated disorders, as defined by DSM-IV, in a subject in need thereof, the method comprising administering cannabidivarin to the subject, wherein the one or more symptoms or disease characteristics are one or more of: (i) qualitative impairment in social interaction; (ii) qualitative impairment in communication; and (iii) restricted repetitive and stereotyped patterns of behaviour interest and activities.

2. The method according to claim 1, wherein the symptoms or disease characteristics of (i) qualitative impairment in social interaction include one or more of: (a) marked impairment in the use of multiple nonverbal behaviours; (b) failure to develop peer relationships appropriate to developmental level; (c) a lack of spontaneous seeking to share enjoyment, interests, or achievements with other people; and (d) lack of social or emotional reciprocity.

3. The method according to claim 1, wherein the symptoms or disease characteristics of (ii) qualitative impairment in communication include one or more of: (a) delay in, or total lack of, the development of spoken language (not accompanied by an attempt to compensate through alternative modes of communication such as gesture or mime); (b) in individuals with adequate speech, marked impairment in the ability to initiate or sustain a conversation with others;

(c) stereotyped and repetitive use of language or idiosyncratic language; and (d) lack of varied, spontaneous make-believe play or social imitative play appropriate to developmental level.

4. The method according to claim 1, wherein the symptoms or disease characteristics of (iii) restricted repetitive and stereotyped patterns of behaviour interest and activities include one or more of: (a) encompassing preoccupation with one or more stereotyped and restricted patterns of interest that is abnormal either in intensity or focus; (b) apparently inflexible adherence to specific, non-functional routines or rituals; (c) stereotyped and repetitive motor mannerisms; and (d) persistent preoccupation with parts of objects.

5. The method according to claim 1, wherein the symptoms or disease characteristics associated with autistic spectrum disorder comprise two or more symptoms associated with (i) qualitative impairment in social interaction; one or more symptoms associated with (ii) qualitative impairment in communication, and one or more symptoms associated with (iii) restricted repetitive and stereotyped patterns of behavior interest and activities.

6. A method of treating one or more symptoms or disease characteristics associated with autistic spectrum disorder (ASD) or ASD-associated disorders, as defined by DSM-V, in a subject in need thereof, the method comprising administering cannabidivarin to the subject, wherein the one or more symptoms or disease characteristics are one or more of: (a) persistent deficits in social communication and social interaction across contexts, not accounted for by general developmental delays, and (b) restricted, repetitive patterns of behaviour, interests, or activities.

7. The method according to claim6, wherein the symptoms or disease characteristics of (a) persistent deficits in social communication and social interaction across contexts, not accounted for by general developmental delays include one or more of: (i) deficits in social-emotional reciprocity; (ii) deficits in nonverbal communicative behaviours used for social interaction; and (iii) deficits in developing and maintaining relationships.

8. The method according to claim 6, wherein the symptoms or disease characteristics of (b) restricted, repetitive patterns of behaviour, interests, or activities include one or more of: (i) stereotyped or repetitive speech, motor movements, or use of objects; excessive adherence to routines, (ii) ritualized patterns of verbal or nonverbal behaviour, or excessive resistance to change; (iii) highly restricted, fixated interests that are abnormal in intensity or focus; and (iv) hyper-or hypo-reactivity to sensory input or unusual interest in sensory aspects of environment.

9. The method according to claim 6 wherein the symptoms or disease characteristics associated with autistic spectrum disorder comprise all three of (i) deficits in social-emotional reciprocity; (ii) deficits in nonverbal communicative behaviours used for social interaction; and (iii) deficits in developing and maintaining relationships together with two or more of (i) stereotyped or repetitive speech, motor movements, or use of objects; excessive adherence to routines, (ii) ritualized patterns of verbal or nonverbal behaviour, or excessive resistance to change; (iii) highly restricted, fixated interests that are abnormal in intensity or focus; and (iv) hyper-or hypo-reactivity to sensory input or unusual interest in sensory aspects of environment.

10. The method according to claim 1, wherein the ASD-associated disorder is Fragile X syndrome.

11. The method according to claim 1, wherein the ASD-associated disorder is Rett syndrome.

12. The method according to claim 1, wherein the ASD-associated disorder is Angelman syndrome.

13. The method according to claim 6, wherein the ASD-associated disorder is Fragile X syndrome.

14. The method according to claim 6, wherein the ASD-associated disorder is Rett syndrome.

15. The method according to claim 6, wherein the ASD-associated disorder is Angelman syndrome.

16. The method according to claim 2, wherein the (a) marked impairment in the use of multiple nonverbal behaviours is one or more of eye-to-eye gaze, facial expression, body postures, and gestures to regulate social interaction.

17. The method according to claim 2, wherein the (c) a lack of spontaneous seeking to share enjoyment, interests, or achievements with other people is a lack of showing, bringing, or pointing out objects of interest.

18. The method according to claim 4, wherein the (c) stereotyped and repetitive motor mannerisms are one or more of hand or finger flapping or twisting or complex whole-body movements.

\* \* \* \* \*

UNITED STATES PATENT AND TRADEMARK OFFICE
CERTIFICATE OF CORRECTION

PATENT NO. : 11,752,111 B2  
APPLICATION NO. : 16/092374  
DATED : September 12, 2023  
INVENTOR(S) : Geoffrey Guy et al.

Page 1 of 1

It is certified that error appears in the above-identified patent and that said Letters Patent is hereby corrected as shown below:

In the Claims

Claim 7, Column 29, Line 33, "The method according to claim6" should read --The method according to claim 6--.

Signed and Sealed this  
Eighth Day of October, 2024

Katherine Kelly Vidal  
*Director of the United States Patent and Trademark Office*